(12) United States Patent
Paz Briz et al.

(10) Patent No.: US 9,546,351 B2
(45) Date of Patent: Jan. 17, 2017

(54) METHOD AND SYSTEM FOR PROCESSING BIOMASS

(75) Inventors: Fernando Roberto Paz Briz, Quevedo (EC); Fernando Roberto Paz Alcazar, Quevedo (EC)

(73) Assignee: INDUSTRIAS CENTLI, S.A. DE C.V., Monterrey, N.L. (MX)

( * ) Notice: Subject to any disclaimer, the term of this patent is extended or adjusted under 35 U.S.C. 154(b) by 867 days.

(21) Appl. No.: 12/758,291

(22) Filed: Apr. 12, 2010

(65) Prior Publication Data

US 2011/0250635 A1     Oct. 13, 2011

(51) Int. Cl.
  *C12M 1/00*     (2006.01)
(52) U.S. Cl.
  CPC ..................... *C12M 45/04* (2013.01)
(58) Field of Classification Search
  CPC ..... A23L 1/0522; A23L 1/1016; A23L 1/1025
  USPC .......................................................... 426/7
  See application file for complete search history.

(56) References Cited

U.S. PATENT DOCUMENTS

| | | |
|---|---|---|
| 2,752,097 A | 6/1956 | Lecher |
| 3,244,361 A | 4/1966 | Lundahl |
| 3,503,803 A | 3/1970 | Bennett et al. |
| 3,533,567 A * | 10/1970 | Willems ............ 241/163 |
| 4,011,027 A | 3/1977 | Selder |
| 4,211,744 A | 7/1980 | Boucher |
| 4,416,701 A | 11/1983 | Huster et al. |
| 4,619,406 A | 10/1986 | Fishgal |
| 4,802,897 A | 2/1989 | Johnson |
| 4,938,622 A | 7/1990 | Stoerzbach |
| 4,989,988 A | 2/1991 | Hutter et al. |

(Continued)

FOREIGN PATENT DOCUMENTS

| | | |
|---|---|---|
| CN | 1032629 A | 5/1989 |
| CN | 2211855 Y | 11/1995 |

(Continued)

OTHER PUBLICATIONS

STIC Search.*

(Continued)

*Primary Examiner* — D. Lawrence Tarazano
*Assistant Examiner* — Stephanie Cox
(74) *Attorney, Agent, or Firm* — Stinson Leonard Street LLP

(57) ABSTRACT

A method and system for processing biomass. The method uses an apparatus with a housing, a rotor inside of the housing, and a plurality of protrusions extending from the rotor. The method includes placing the biomass in a fluid medium, inducing cavitation within the fluid to partially separate the biomass, sending the biomass and fluid into the housing, rotating the rotor to further separate the biomass, heating the biomass and fluid, and maintaining the acidity of the fluid and biomass at a pH of between approximately 2 to 6. The system includes apparatus each having a housing and a rotor within the housing. One apparatus has abutting, alternating height protrusions extending from the rotor. Another apparatus has grooves formed in the rotor and an end wall of the housing. Another apparatus has two rows of protrusions extending from the rotor that are spaced apart no less than approximately 6 millimeters.

36 Claims, 22 Drawing Sheets

(56) References Cited

U.S. PATENT DOCUMENTS

| | | | |
|---|---|---|---|
| D320,851 S | 10/1991 | Storzbach | |
| 5,203,515 A | 4/1993 | Stoerzbach | |
| 5,358,725 A | 10/1994 | Izumitani et al. | |
| 5,492,654 A | 2/1996 | Kozjuk et al. | |
| 5,717,181 A | 2/1998 | Colgate | |
| 5,810,052 A | 9/1998 | Kozyuk | |
| 5,914,027 A | 6/1999 | Ellingsen | |
| 5,931,771 A | 8/1999 | Kozyuk | |
| 5,937,906 A | 8/1999 | Kozyuk | |
| 5,969,207 A | 10/1999 | Kozyuk | |
| 5,971,601 A | 10/1999 | Kozyuk | |
| 6,012,492 A | 1/2000 | Kozyuk | |
| 6,019,947 A | 2/2000 | Kucherov | |
| 6,035,897 A | 3/2000 | Kozyuk | |
| 6,365,555 B1 | 4/2002 | Moser et al. | |
| 6,502,979 B1 | 1/2003 | Kozyuk | |
| 6,589,501 B2 | 7/2003 | Moser et al. | |
| 6,802,639 B2 | 10/2004 | Kozyuk | |
| 6,857,774 B2 | 2/2005 | Kozyuk | |
| 6,869,586 B1 | 3/2005 | Moser et al. | |
| 7,041,144 B2 | 5/2006 | Kozyuk | |
| 7,086,777 B2 | 8/2006 | Kozyuk | |
| 7,178,975 B2 | 2/2007 | Kozyuk | |
| 7,207,712 B2 | 4/2007 | Kozyuk | |
| 7,247,244 B2 | 7/2007 | Kozyuk | |
| 7,314,306 B2 | 1/2008 | Kozyuk | |
| 7,314,516 B2 | 1/2008 | Kozyuk et al. | |
| 7,338,551 B2 | 3/2008 | Kozyuk | |
| 7,357,566 B2 | 4/2008 | Kozyuk | |
| 7,452,425 B1 | 11/2008 | Langhauser | |
| 2002/0074284 A1* | 6/2002 | Low | 210/511 |
| 2003/0108460 A1* | 6/2003 | Andreev et al. | 422/186.07 |
| 2004/0022122 A1 | 2/2004 | Kozyuk | |
| 2004/0042336 A1 | 3/2004 | Kozyuk | |
| 2005/0118692 A1* | 6/2005 | Kinley et al. | 435/161 |
| 2005/0136520 A1* | 6/2005 | Kinley et al. | 435/155 |
| 2005/0186315 A1 | 8/2005 | Liyama et al. | |
| 2005/0233030 A1 | 10/2005 | Lewis et al. | |
| 2005/0237855 A1 | 10/2005 | Kozyuk | |
| 2006/0050608 A1 | 3/2006 | Kozyuk | |
| 2006/0081501 A1 | 4/2006 | Kozyuk | |
| 2006/0088630 A1 | 4/2006 | Fox et al. | |
| 2006/0187748 A1 | 8/2006 | Kozyuk | |
| 2006/0251829 A1 | 11/2006 | Braun et al. | |
| 2006/0283788 A1 | 12/2006 | Schreppel, Jr. | |
| 2007/0193874 A1 | 8/2007 | Adiga et al. | |
| 2008/0011597 A1 | 1/2008 | Spani | |
| 2008/0144431 A1 | 6/2008 | Troxler | |
| 2008/0277264 A1 | 11/2008 | Sprague | |
| 2008/0277354 A1 | 11/2008 | Baerheim et al. | |
| 2008/0281131 A1 | 11/2008 | Kozyuk | |
| 2009/0098266 A1 | 4/2009 | Briz et al. | |
| 2009/0186383 A1 | 7/2009 | Mancosky | |
| 2010/0012583 A1 | 1/2010 | Stuart | |
| 2010/0112125 A1 | 5/2010 | Kozyuk | |

FOREIGN PATENT DOCUMENTS

| | | |
|---|---|---|
| CN | 1671301 | 9/2005 |
| GB | 702811 | 1/1954 |
| GB | 2382787 | 6/2003 |
| JP | 2006-167623 | 6/2006 |
| JP | 2007-028972 | 2/2007 |
| KR | 10-2001-0069836 | 7/2001 |
| WO | WO 98/11983 | 3/1998 |
| WO | WO 2004/008850 | 1/2004 |
| WO | WO 2005/058073 A1 | 6/2005 |
| WO | WO 2006/066421 A1 | 6/2006 |
| WO | WO 2008/068572 | 6/2008 |

OTHER PUBLICATIONS

Chinese Patent Office; The First Office Action; CN Patent Application No. 200880120052.5; Jan. 18, 2012.

Kinematica AG, Megatron System MT 5000, pp. 1-6, Dec. 2002, Switzerland.

Kinematica AG, Megatron System MT-V 1-65/MT-V 3-65, pp. 1-4, May 2003, Switzerland.

Kinematica AG, Megatron System MT 3000, pp. 1-4, Nov. 2002, Switzerland.

European Nano Systems 2005, Thomas Hielscher, Ultrasonic Production of Nano-Size Dispersions & Emulsions, pp. 138-143, Dec. 2005, Paris, France.

International Search Report and Written Opinion for PCT Patent Application No. PCT/MX08/000137, dated Feb. 19, 2009, 10 pages.

Suarez, Y., "Diseno Conceptual Y Comparacion Tecnica De Los Procesos De Hidrolisis Acida Y Enzimatica Para La Produccion de Glucosa A Partir de Almidon de Yuca", Universidad Industrial De Santander, Facultad de Ciencias Fisicoquimicas, Escuela de Ingenieria Quimica, Bucaramanga (2004) (116 pgs) http://repositorio.uis.edu.co/jspui/bitstream/123456789/6561/2/114533.pdf.

Perry, R.H. & Green, D.W., Perry's Chemical Engineers' Handbook, 1984, pp. 4-24 to 4-28, Sixth Edition, McGraw-Hill, United States.

* cited by examiner

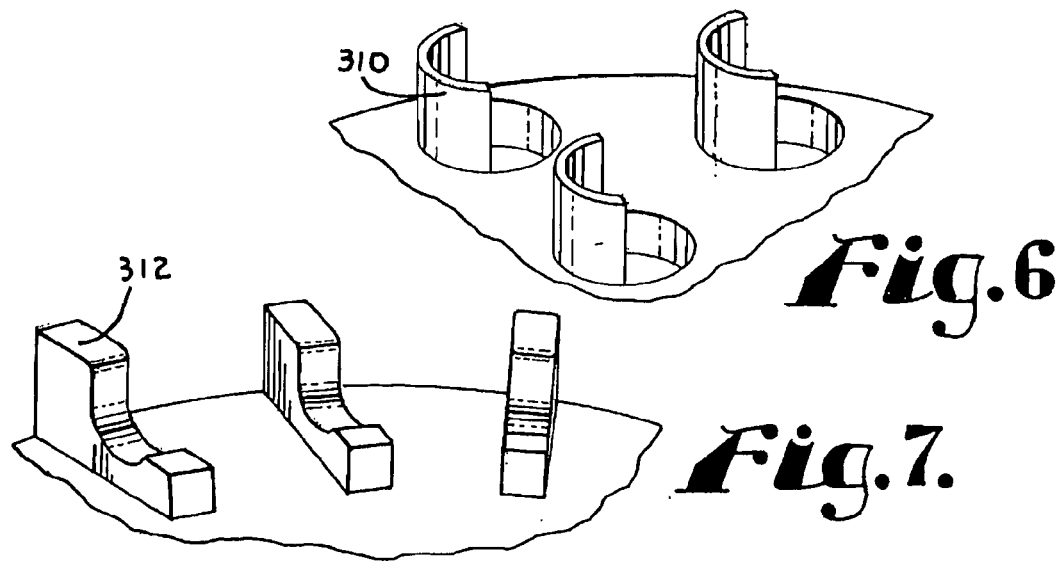
Fig.6.
Fig.7.
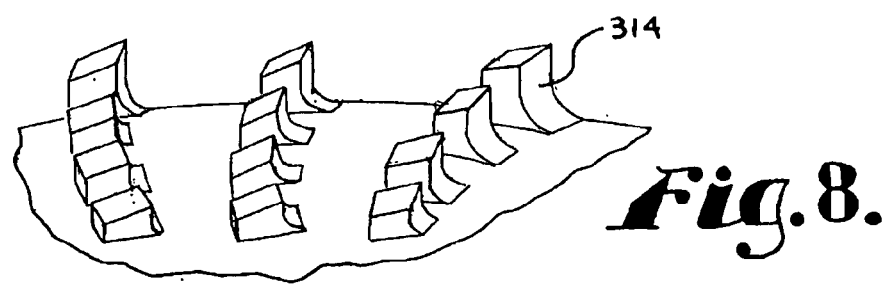
Fig.8.
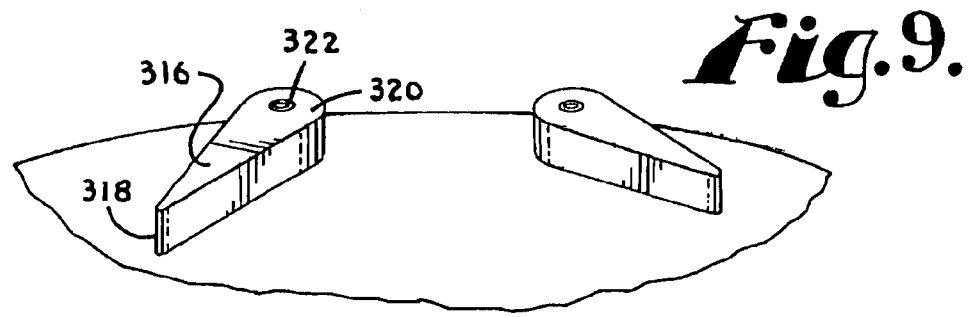
Fig.9.

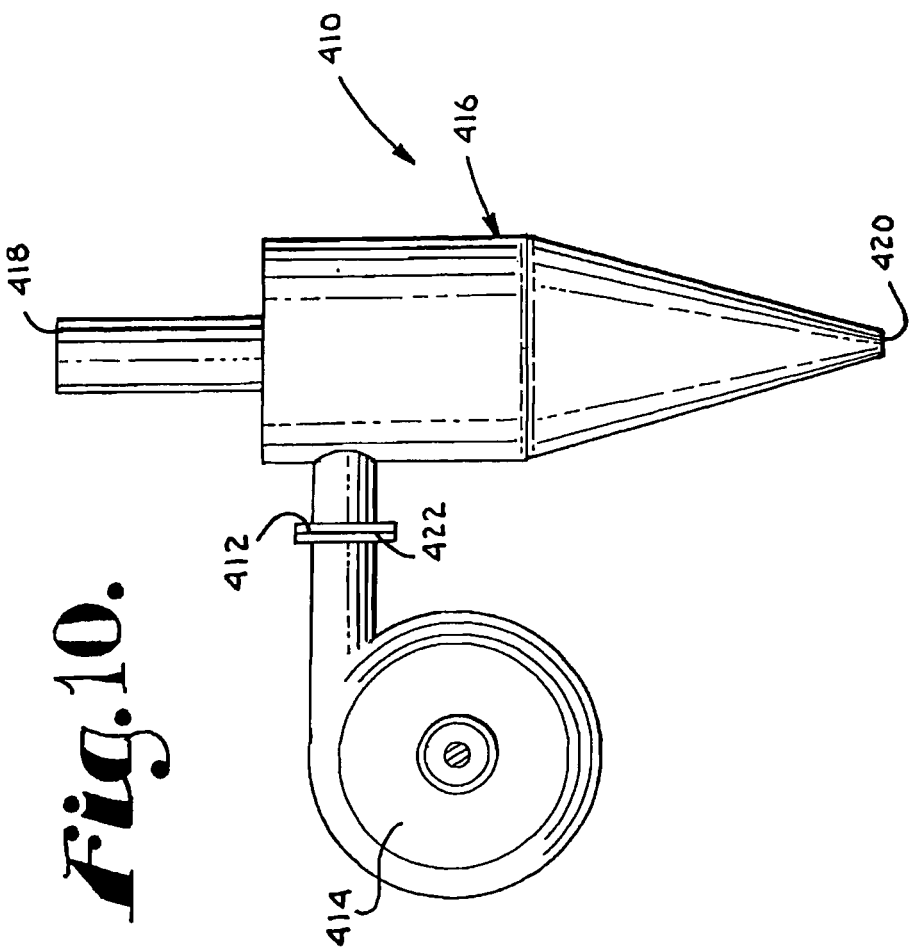

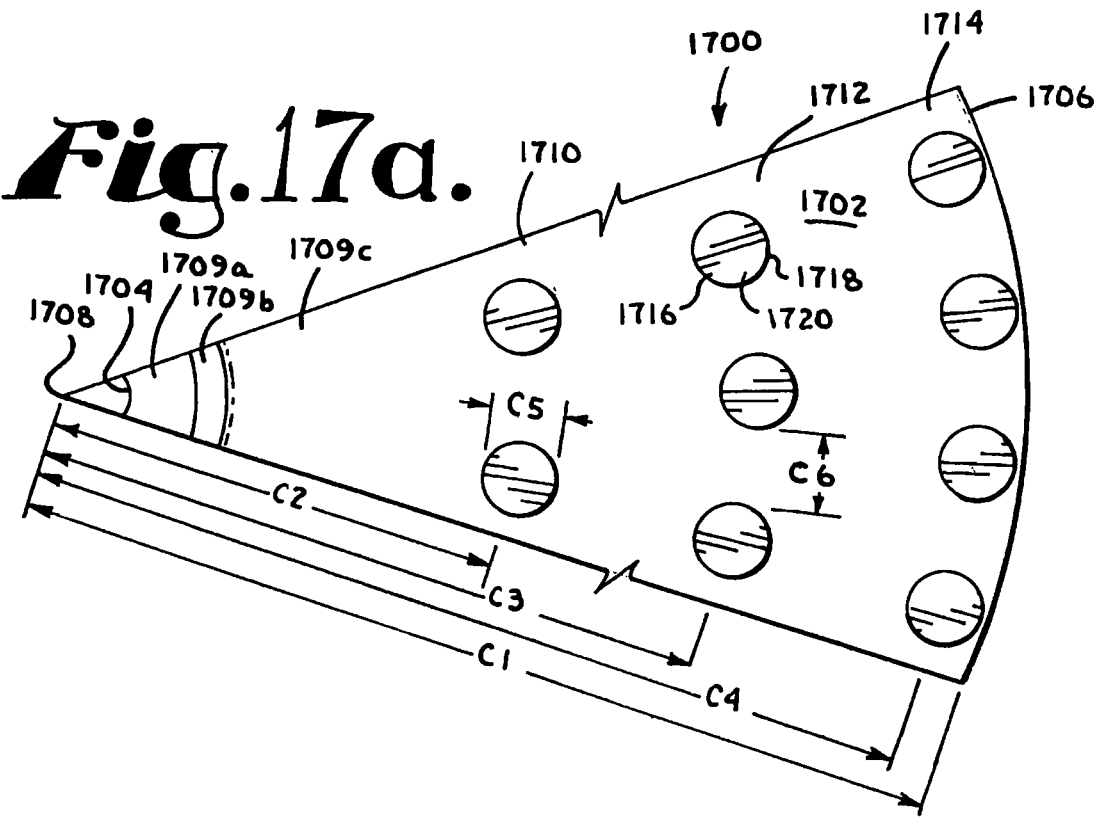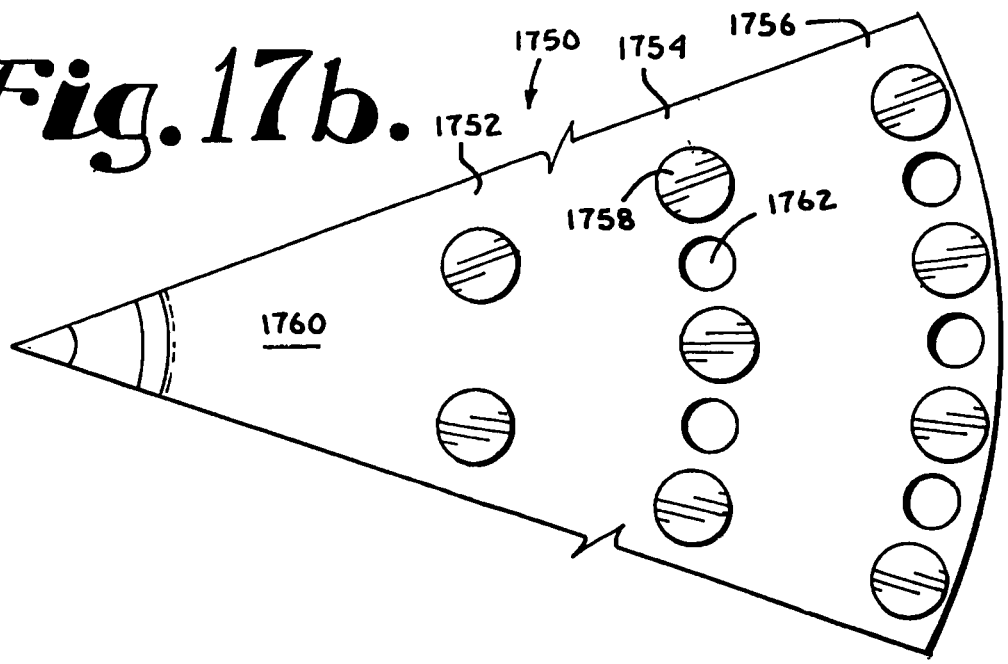

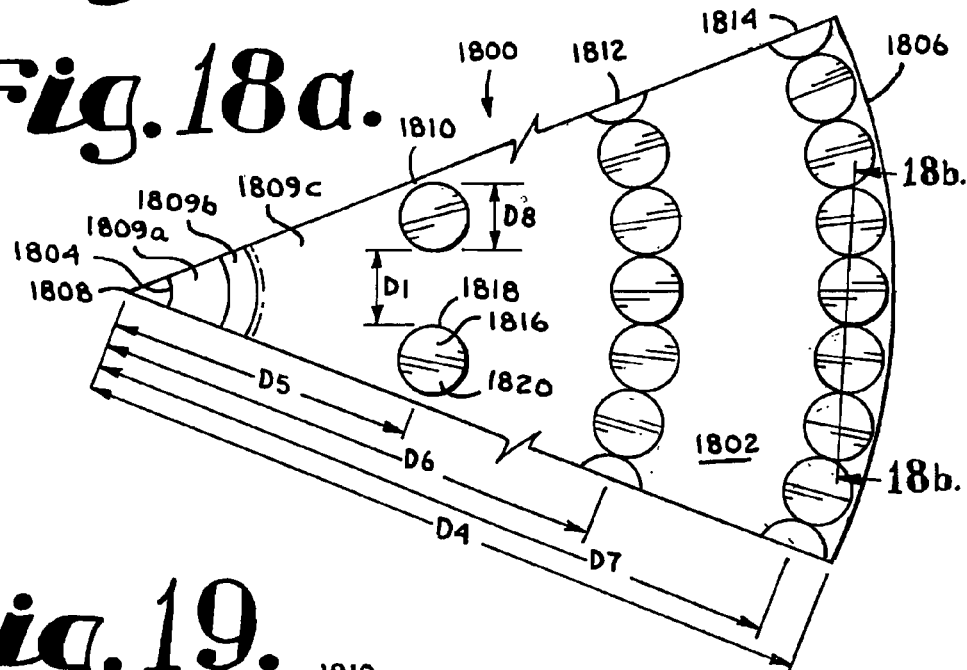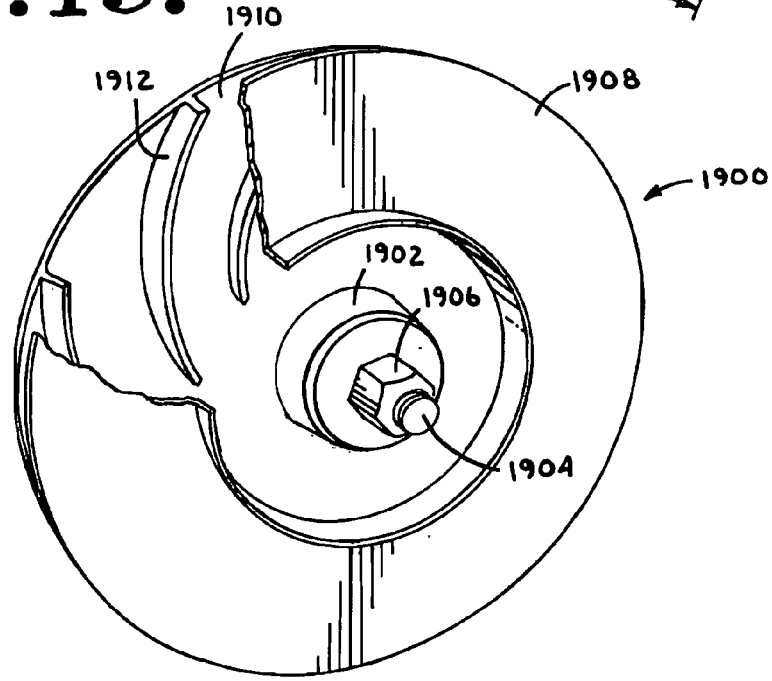

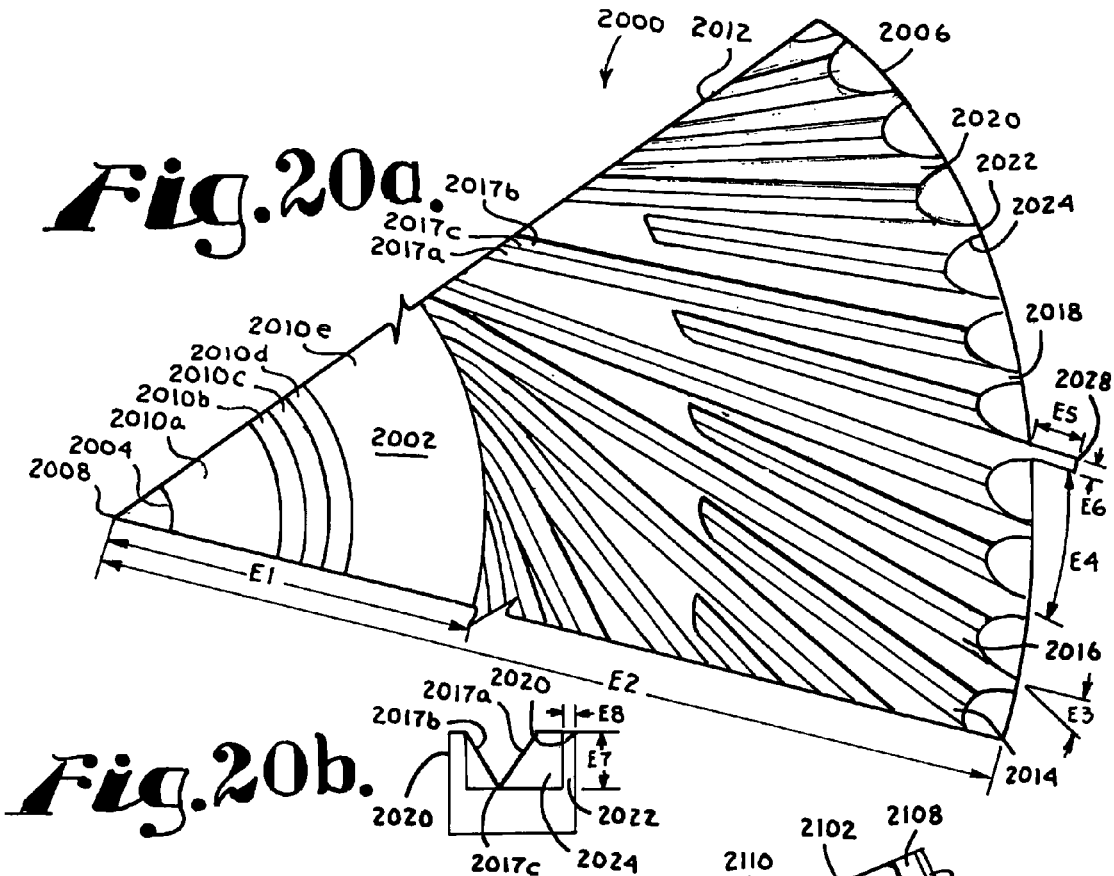
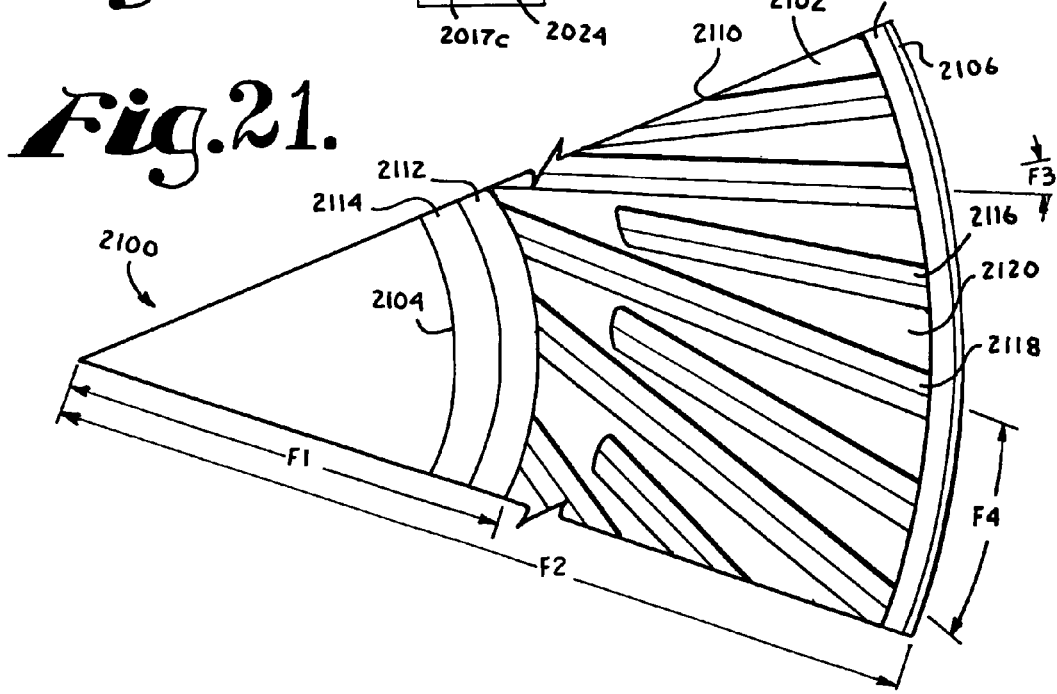

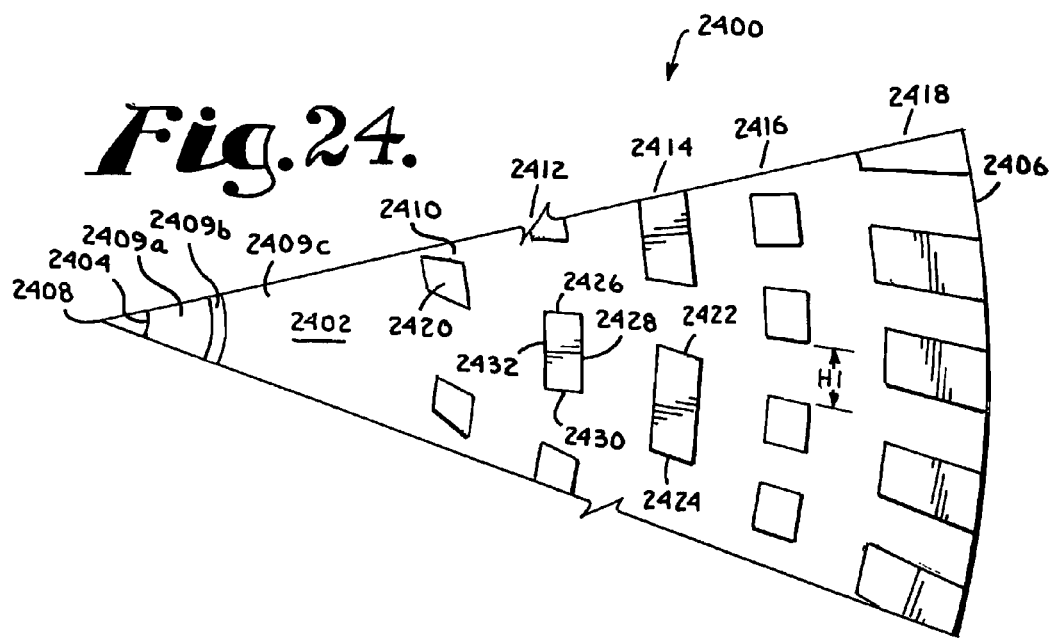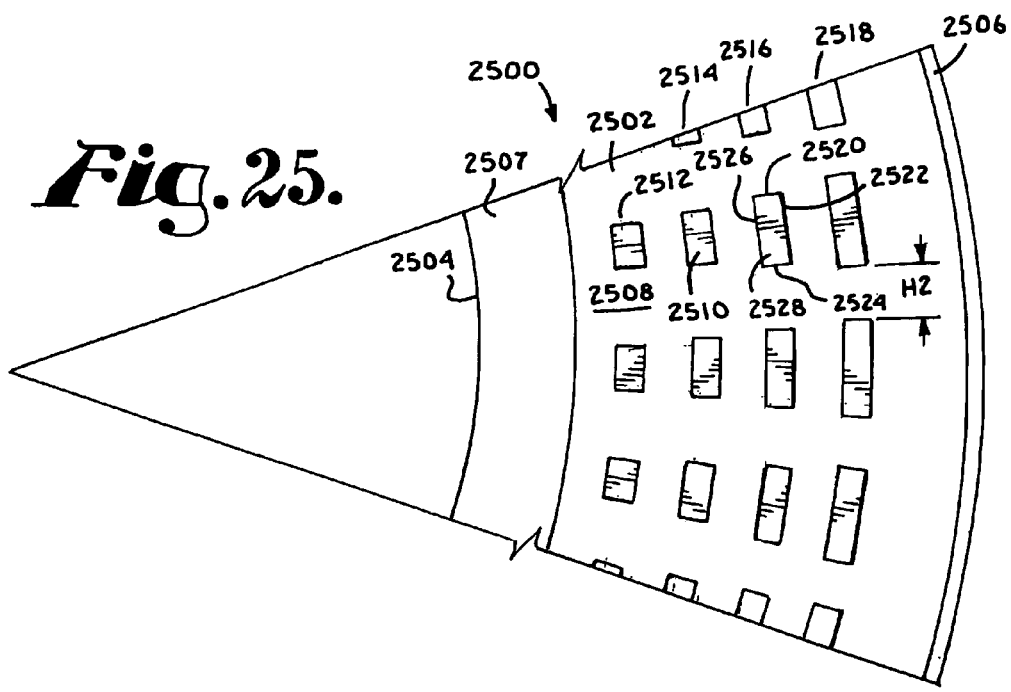

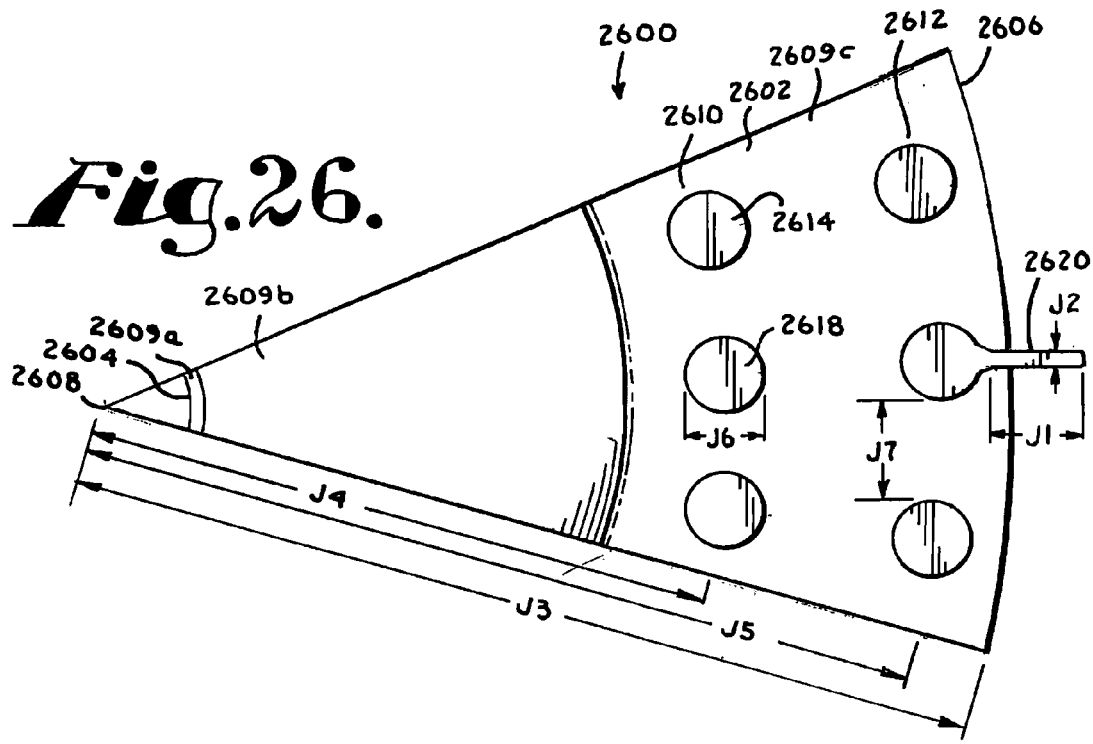
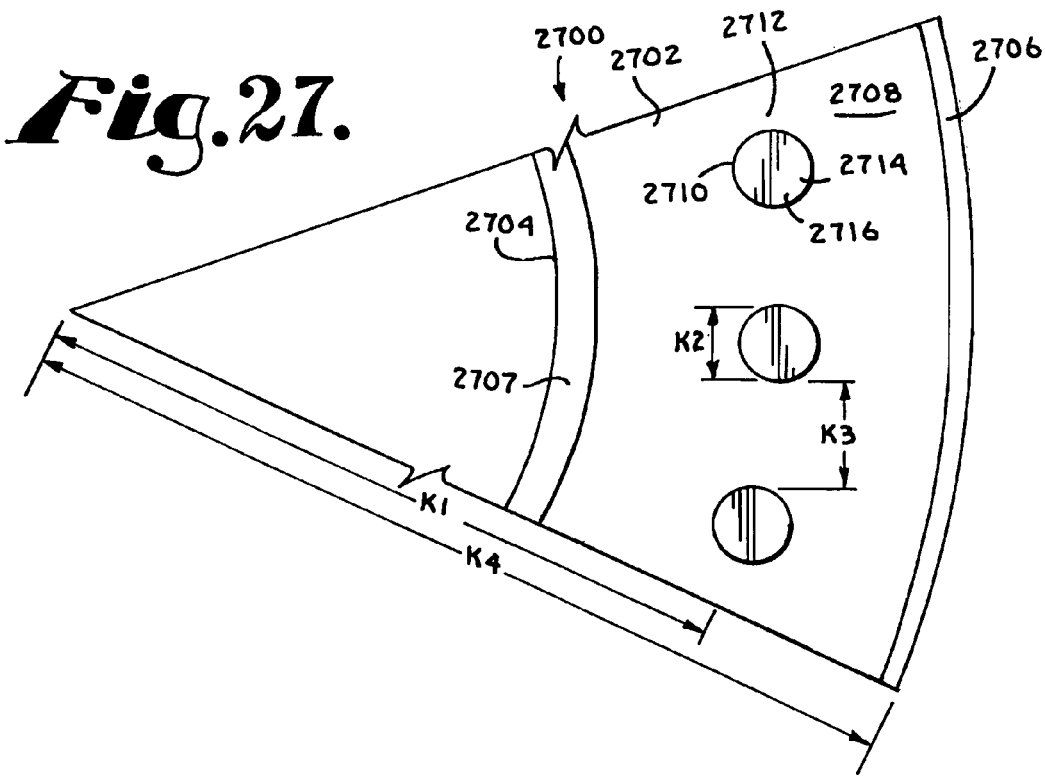

METHOD AND SYSTEM FOR PROCESSING BIOMASS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention is related in general to a method and system for processing biomass and more particularly to a method and system for processing corn.

2. Description of Related Art

It has long been desirable to quickly separate joined components without degradation of the individual components. Examples of joined components needing separation include grain components, contaminants from pure products, juice from solid biomass, and starch and protein from biomass. Corn, in particular, is a grain that is desirable to separate into its individual components without degrading the components. Corn endosperm is rich in starch and protein which are both valuable as separate components.

A typical process for separating or milling corn includes fermenting (steeping) the kernels in warm water and sulfur dioxide for about 35 to 50 hours. The fermentation process softens the corn for easier separation by mechanical processing, but it also degrades the components of the corn. Some of the components of the kernels typically dissolve or suspend in the acidic water and are subsequently discarded. Discarding these components results in less profit for the corn miller. Additionally, at the end of the milling process, the corn requires substantial drying due to the fermentation process.

After fermentation, a degerminator separates the germ, pericarp and endosperm through abrasion between the corn and degerminator, abrasion between the individual corn kernels and impact between the corn and degerminator. Conventional degerminators frequently break the germ and do not consistently provide complete separation of germ and endosperm. Conventional degerminators also do not separate the starch and protein within the endosperm. Thus, a typical corn milling process is relatively expensive, time consuming and inefficient.

BRIEF SUMMARY OF THE INVENTION

The invention claimed herein is a method and apparatus for processing biomass. The method for processing biomass uses an apparatus comprising a housing presenting a chamber having an inlet, an outlet, and a shaft opening. A shaft projects through the opening. A rotor is coupled with the shaft inside the chamber. A plurality of protrusions extend from the rotor. The method comprises the steps of placing the biomass in a fluid medium, inducing cavitation within the fluid to at least partially separate the biomass, sending the biomass and fluid through the inlet, rotating the rotor to further separate the biomass, and maintaining the acidity of the fluid at a pH of between approximately 2 to 6.

The method preferably comprises the additional steps of maintaining the acidity of the fluid at a pH of between approximately 3.8 to 4.5 and maintaining the temperature of the fluid and biomass between approximately 30 to 52 degrees Celsius. Preferably, the biomass is separated by inducing cavitation within the fluid, inducing abrasion among the biomass, inducing abrasion between the biomass and the fluid, subjecting the biomass to centrifugal force, and impacting the biomass with the protrusions.

Preferably, the biomass processing method is used to separate the endosperm, germ, and pericarp of corn kernels into a separate endosperm stream and a germ and pericarp stream. Then, the method separates the starch and protein molecules within the endosperm stream so that they may later be divided into relatively pure separate starch and protein streams.

The biomass processing system comprises an apparatus for separating joined components present in a fluid medium. The apparatus has a housing presenting a chamber comprising an inlet, an outlet and a shaft opening. A shaft projects through the shaft opening. A rotor is coupled with the shaft inside the chamber. A plurality of protrusions extend from the rotor. The protrusions are spaced approximately equidistant from a center of the rotor. Adjacent protrusions abut each other. The protrusions comprise first and second sets of alternating protrusions having first and second heights, respectively, the first height being greater than the second height.

An alternative embodiment of apparatus has a housing presenting first and second end walls and a side wall defining a chamber, an inlet in the first end wall, an outlet in the side wall, and a shaft opening in the second end wall. A shaft projects through the shaft opening. A rotor is coupled with the shaft inside the chamber. The rotor presents a front surface facing the inlet and has a plurality of grooves formed in the front surface. A plurality of grooves are formed in the first end wall of the housing also.

An alternative embodiment of apparatus has a housing presenting a chamber comprising an inlet, an outlet and a shaft opening. A shaft projects through the shaft opening. A rotor is coupled with the shaft inside the chamber. A plurality of protrusions extend from the rotor. The protrusions comprises a first row spaced approximately equidistant from a center of the rotor, and a second row spaced approximately equidistant from the first row. The protrusions in the rows are spaced apart no less than approximately 6 millimeters.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 6 is a perspective view of a portion of a rotor with C-shaped protrusions;

FIG. 7 is a perspective view of a portion of a rotor with J-shaped protrusions;

FIG. 8 is a perspective view of a portion of a rotor having tooth-like protrusions arranged in an arc;

FIG. 9 is a perspective view of a portion of a rotor having rotational protrusions;

FIG. 10 is a front elevational view of an alternative embodiment of an apparatus according to the present invention, showing a hydrocyclone coupled with the housing outlet;

FIG. 17A is a front elevational view of a rotor having three rows of cylindrical protrusions;

FIG. 17B is a front elevational view of a rotor having three rows of cylindrical protrusions with holes between some of the protrusions;

FIG. 18A is a front elevational view of a rotor having three rows of cylindrical protrusions with some protrusions abutting;

FIG. 18B is a cross sectional view taken through the line 18B-18B in FIG. 18A;

FIG. 19 is a perspective view of a closed rotor;

FIG. 20A is a front elevational view of a rotor having grooves;

FIG. 20B is a side elevational view of a portion of the grooves on the rotor in FIG. 20A;

FIG. 21 is a front elevational view of a housing end wall configuration having grooves;

FIG. 24 is a front elevational view of a rotor having five rows of protrusions each having a polygonal cross-section;

FIG. 25 is a front elevational view of a housing end wall configuration having four rows of protrusions each having a polygonal cross-section;

FIG. 26 is a front elevational view of a rotor having two rows of cylindrical protrusions;

FIG. 27 is a front elevational view of a housing end wall configuration having one row of cylindrical protrusions;

DETAILED DESCRIPTION OF PREFERRED EMBODIMENT

Figure 1:
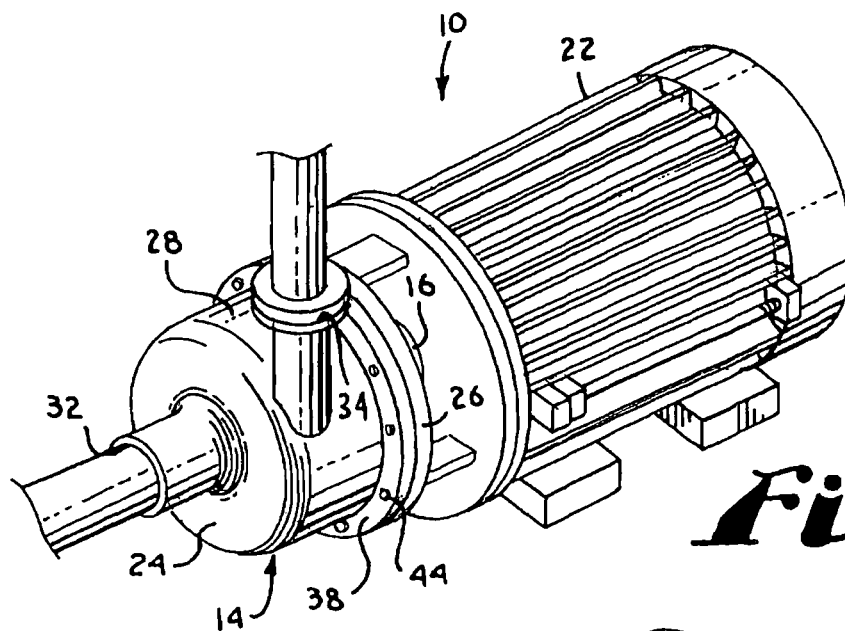
FIG. 1 is a perspective view of an apparatus according to the present invention.
Figure 2:
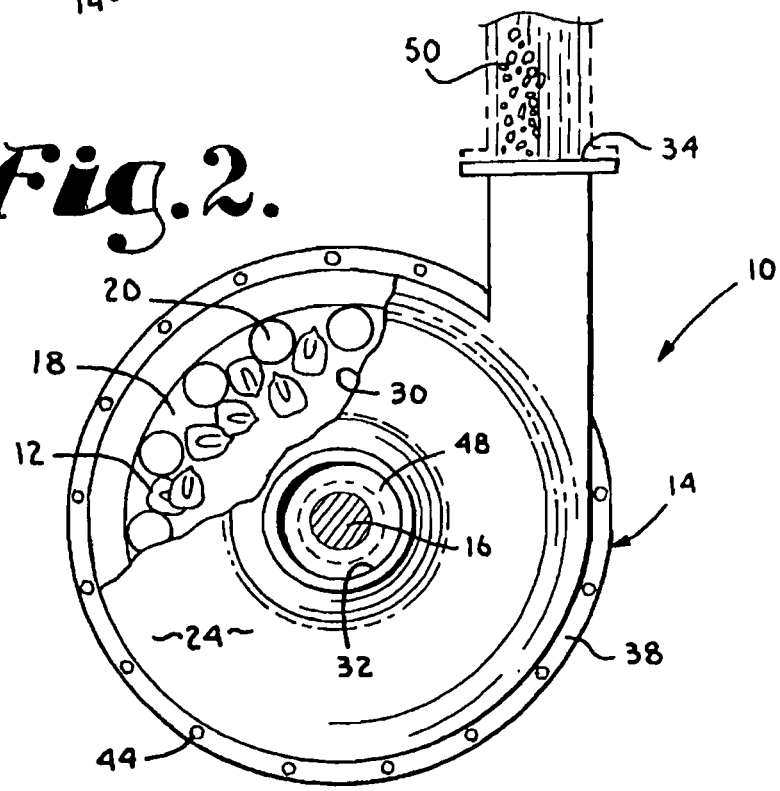
FIG. 2 is a front elevational view, with portions broken away, of the apparatus of FIG. 1.
Figure 3:
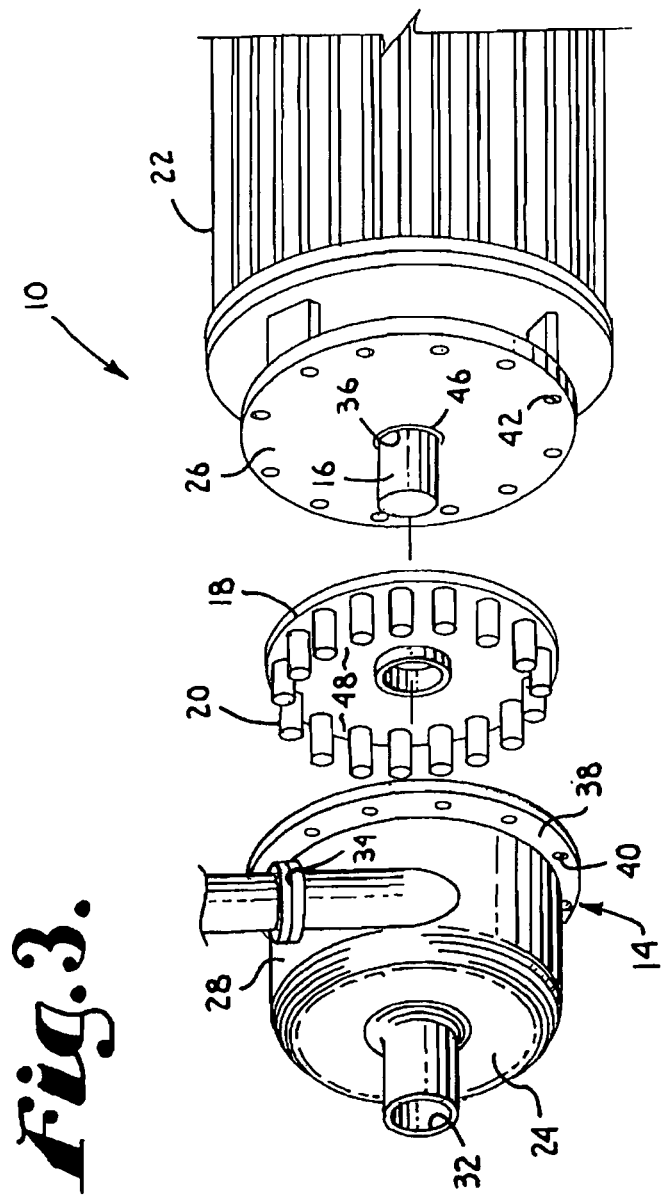
FIG. 3 is an exploded perspective view of the apparatus of FIG. 1.

FIGS. 1-3 show an apparatus 10 adapted to separate joined components placed in a fluid medium, purify liquid, promote interaction between two or more components placed in a fluid medium, and improve combustion of a liquid fuel. FIG. 2 shows the apparatus separating joined components. The joined components shown are the endosperm, germ and pericarp of corn kernels 12. Although FIG. 2 shows apparatus 10 separating corn, any joined component may be separated by the apparatus. Further, although FIG. 2 shows apparatus functioning as a separator, the apparatus also purifies liquid, promotes interaction between two or more components, and improves combustion of a liquid fuel. FIGS. 1-3 show the apparatus with a housing 14, a shaft 16, a circular rotor 18, protrusions 20 extending from rotor 18, and a motor 22 coupled with shaft 16.

FIGS. 2 and 3 show housing 14 with a first end wall 24, a second end wall 26, and a side wall 28 defining an interior cavitation chamber 30. FIGS. 1-3 show housing 14 with an inlet 32 in first end wall 24 adapted to allow fluid and components to enter chamber 30, and an outlet 34 in side wall 28 adapted to allow fluid and components to exit chamber 30. Inlet 32 may be coupled with a hopper (not shown) containing components, liquid or both. FIG. 3 shows a shaft opening 36 in second end wall 26. Shaft 16 projects into chamber 30 through shaft opening 36. FIGS. 1-3 show a flange 38 extending from side wall 28. FIG. 3 shows openings 40 in flange 38 which are aligned with openings 42 in second end wall 26. FIG. 1 shows bolts 44 securing flange 38 with second end wall 26. A seal (not shown) is preferably placed between flange 38 and second end wall 26, and a seal 46, shown in FIG. 3, is placed between shaft 16 and second end wall 26 to prevent fluid from leaking out of chamber 30.

FIG. 2 shows rotor 18 coupled with shaft 16 inside chamber 30. Rotor 18 has a front surface 48 facing inlet 32. Cylindrical protrusions 20 extend from front surface 48 toward inlet 32. All of the protrusions 20 are equidistant from the center of rotor 18 adjacent the peripheral edge of front surface 48. The spacing between adjoining protrusions 20 determines the length of time that components are retained within chamber 30. Protrusions spaced closer together will retain components within the chamber for a longer period of time than protrusions spaced farther apart. The longer the components are retained within the chamber, the greater the likelihood that the components will separate or interact, whichever is preferred. Preferably, the protrusions are spaced a distance sufficient to retain components within the housing or chamber until the components separate or interact. FIG. 2 shows adjoining protrusions 20 spaced a distance sufficient to retain corn kernels 12 within chamber 30 until separation of the germ, pericarp and endosperm. Preferably, the space between adjoining protrusions 20 is approximately 6 to 12 millimeters. The spacing between protrusions also affects the number of impacts between the components and the protrusions. More impacts between the components and the protrusions occur as the protrusions are spaced closer together. Therefore, if less impacts are desired the distance between protrusions should be increased. Although cylindrical protrusions 20 mounted equidistant from the rotor's center are shown, any type of protrusions mounted in any pattern on the rotor are within the scope of the invention.

FIG. 2 shows separation of the endosperm, germ and pericarp of corn kernels 12 placed in a fluid medium. Motor 22, shown in FIGS. 1 and 3, rotates shaft 16 and rotor 18 at a speed sufficient to cause cavitation within the fluid. The endosperm, germ and pericarp are separated by the combined effects of the rapid creation and implosion of the cavitation bubbles formed within the fluid, abrasion between the fluid and corn components, abrasion between the corn components, impacts between the corn components and protrusions 20, and centrifugal force. Before separation, the corn is retained within housing 14 by protrusions 20. While the corn is retained by protrusions 20, the fluid flows by the corn at high speed causing fluid abrasion on the corn's surface. The corn kernels 12 also rotate with respect to rotor 18 causing abrasion between the kernels. Each kernel 12 also impinges the protrusions 20. All of these factors contribute to separating the corn 12 into its components. FIG. 2 shows the separated components 50 exiting outlet 34. Although separation of corn is shown in FIG. 2, any type of joined component may be separated with apparatus 10, and the apparatus may also be used to purify liquid, promote interaction between two or more components in a fluid medium, and improve combustion of a liquid fuel.

Figure 4:
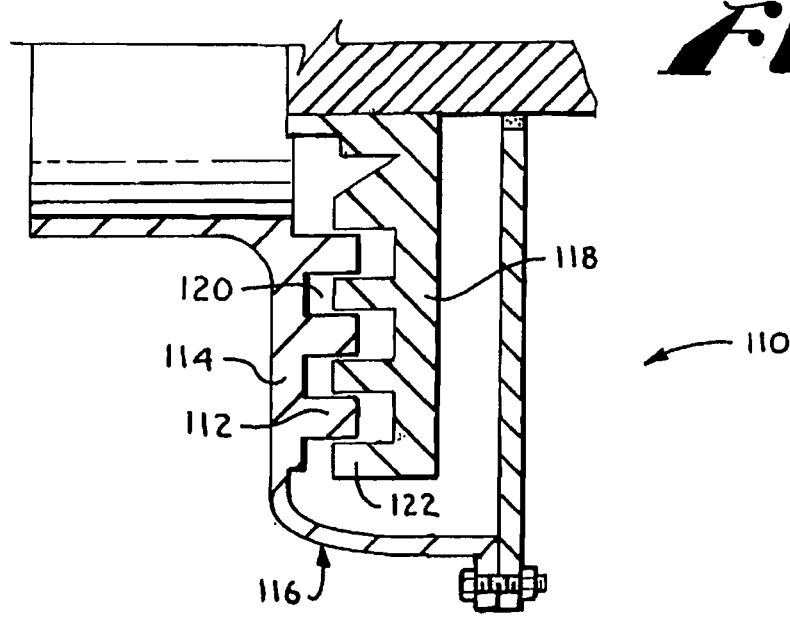
FIG. 4 is a partial cross sectional view of an alternative embodiment of an apparatus according to the present invention, showing a housing having protrusions.

FIG. 4 shows an alternative embodiment of an apparatus 110 according to the present invention. Apparatus 110 is substantially the same as apparatus 10 described above in connection with FIGS. 1-3 except that apparatus 110 has protrusions 112 extending from first end wall 114 of housing 116 toward rotor 118. Three circular rows of protrusions 112 extend from first end wall 114. There are gaps 120 between adjacent rows. Rotor 118 has four rows of protrusions 122 which are spaced a distance from the rotor's center such that the rows align with gaps 120.

Figure 5:
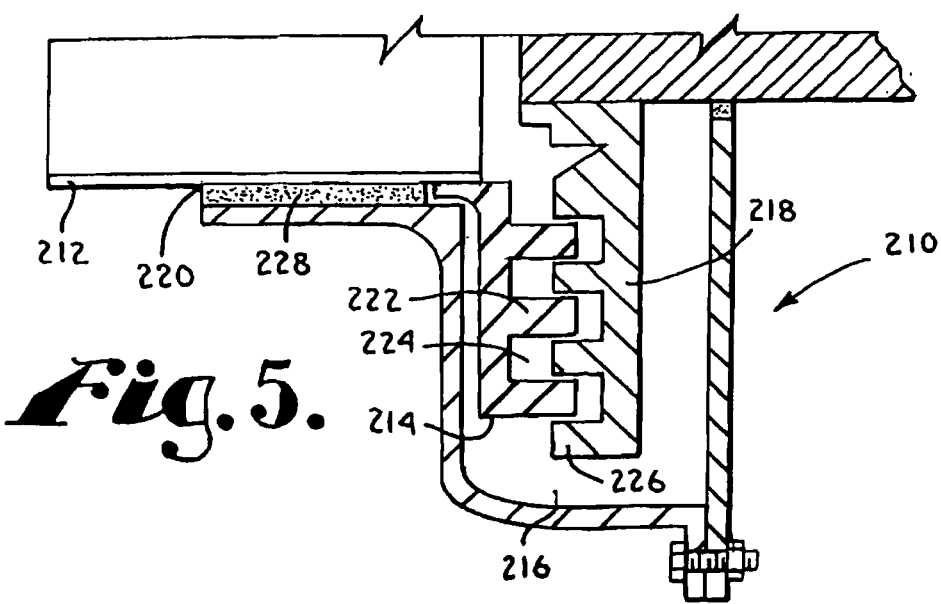
FIG. 5 is a partial cross sectional view of another alternative embodiment of an apparatus according to the present invention, showing a rotor and counter-rotor.

FIG. 5 shows another alternative embodiment of an apparatus 210 according to the present invention. Apparatus 210 is substantially the same as the apparatus 10 described above in connection with FIGS. 1-3 except that apparatus 210 has a tube 212 and a counter-rotor 214 coupled with tube 212 inside of interior chamber 216. Counter-rotor 214 has a front surface facing the front surface of rotor 218. Tube 212 is received by inlet 220 and extends into chamber 216. Three circular rows of protrusions 222 extend from the front surface of counter-rotor 214 toward rotor 218. There are gaps 224 between adjacent rows. Rotor 218 has four rows of protrusions 226 which are spaced a distance from the rotor's center such that the rows align with gaps 224. A seal 228 is positioned between tube 212 and inlet 220 for preventing fluid from leaking out of chamber 216. A drive mechanism (not shown), such as a belt, may be coupled with tube 212 outside chamber 216 for rotating tube 212 and counter-rotor 214. Although apparatuses 110 and 210 are shown in FIGS. 4 and 5 with circular rows of protrusions, the rows on housing, rotor and counter-rotor may have any configuration permitting the rotor to rotate within the housing.

FIGS. 6-9 show examples of protrusions that may be used with any of the apparatuses 10, 110 and 210 described above in connection with FIGS. 1-5. FIG. 6 shows protrusions 310 having a C-shaped top profile. The protrusions are hollow and are arranged in two rows on the rotor. C-shaped protrusions 310 are preferably used when it is desirable to induce high levels of cavitation in the fluid. FIG. 7 shows protrusions 312 having a J-shaped side profile. J-shaped protrusions 312 are positioned adjacent a peripheral edge of the front surface of the rotor. FIG. 8 shows four rows of spaced apart tooth-like protrusions 314. The rows are positioned in offset relationship such that the protrusions 314 form a radial curved pattern. FIG. 9 shows rotating protrusions 316. The protrusions 316 have a free end 318 and a fixed end 320 rotatably mounted on the front surface of the rotor. The fixed end 320 has an opening which receives a pin 322 extending from the rotor. The invention described herein is not limited to any particular type of protrusions, or any particular pattern of protrusions. All protrusions and patterns shown herein are exemplary only.

FIG. 10 shows an alternative embodiment of an apparatus 410 according to the present invention. Apparatus 410 is substantially identical to the apparatuses 10, 110 and 210 described in connection with the embodiments shown in FIGS. 1-5 except that outlet 412 of housing 414 is coupled with a hydrocyclone 416, or centrifuge. Hydrocyclone 416 has the general shape of an inverted cone with a cylinder extending upward from the base of the cone. Hydrocyclone 416 has a top outlet 418, a bottom outlet 420 and an inlet 422 coupled with housing outlet 412. Inlet 422 is positioned near the top of hydrocyclone 416.

In operation, motor 22 of apparatus 10, shown in FIGS. 1-3, is powered on. Inlet 32 receives joined components placed in fluid, unpurified liquid, two or more components placed in fluid, or liquid fuel. The joined components placed in fluid, unpurified liquid, two or more components placed in fluid, or liquid fuel enter chamber 30. Motor 22 rotates shaft 16 and rotor 18 at a speed sufficient to cause cavitation of the fluid within chamber 30 as protrusions 20 move through the fluid. The speed of shaft rotation is preferably between 500 to 10,000 revolutions per minute.

The fluid cavitates due to the reduction in fluid pressure behind protrusions 20 as the protrusions move through the fluid. The fluid cavitates from a liquid to a gas when the fluid pressure behind protrusions 20 is reduced to below the liquid's vapor pressure. A plurality of gas bubbles form within the fluid due to cavitation. These gas bubbles move from the low pressure area of formation into an area of chamber 30 with higher fluid pressure. Upon entering a region of fluid pressure greater than the vapor pressure of the liquid, the gas bubbles collapse. This creation and collapse, or implosion, of gas bubbles creates ultrasonic waves within chamber 30. The power of the ultrasonic waves has been measured at the outside of housing 14 as being between about 40 dB to about 60 dB by a well known cavitation implosion measuring device sold under the trademark Vibrotip®. The ultrasonic waves are a primary factor in separating joined components within a fluid medium, in purifying liquid by killing undesirable organisms within the liquid, in promoting interaction between two or more components, and in improving combustion of liquid fuel by vaporizing the liquid fuel.

Additional forces within chamber 30 contribute to separating joined components within a fluid medium, purifying liquid, promoting interaction between two or more components in a fluid medium, and improving combustion of a liquid fuel. These forces include centrifugal force resulting from rotating rotor 18 within the fluid, abrasion between the fluid and components, abrasion between the components, and impacts between the components and protrusions 20. The combined effects of these factors contribute to separating joined components placed within a fluid, purifying liquid, promoting interaction between two or more components placed within a fluid, and improving combustion of a liquid fuel. The separated components and fluid, purified liquid, interacted components and fluid, or liquid fuel exit chamber 30 through outlet 34.

Apparatus 110 shown in FIG. 4 operates in the same way as described above for apparatus 10 shown in FIGS. 1-3. Apparatus 210 shown in FIG. 5 operates in substantially the same manner as apparatus 10 shown in FIGS. 1-3 except that apparatus 210 has a rotating tube 212 and counter-rotor 214. A drive mechanism (not shown) coupled with tube 212 rotates tube 212 and counter-rotor 214. Tube 212 and counter-rotor 214 preferably rotate in a direction opposite to the direction of rotation of rotor 218, but it is within the scope of the invention for rotor 218 and counter-rotor 214 to rotate in the same direction. The components and fluid enter chamber 216 through tube 212.

Apparatus 410 shown in FIG. 10 has a housing 414 with a rotor that operates in the same manner as any of the apparatuses 10, 110 and 210 described in FIGS. 1-5. However, after the fluid and components exit outlet 412 they enter hydrocyclone 416. Fluid and components exiting outlet 412 and entering hydrocyclone 416 rotate around the interior wall of hydrocyclone 416. The rotation subjects the fluid and components to a centrifugal force which divides the components based on density. Heavier components move outward toward the interior wall of hydrocyclone 416 and spiral down the wall to bottom outlet 420. Lighter components move toward the center axis of hydrocyclone 416 and exit through top outlet 418. Thus, hydrocyclone 416 divides components with different densities. Hydrocyclone 416 is particularly well suited to divide gas from liquid. A slight vacuum may be introduced at top outlet 418 to induce the lighter components to exit through top outlet 418.

Figure 11A:
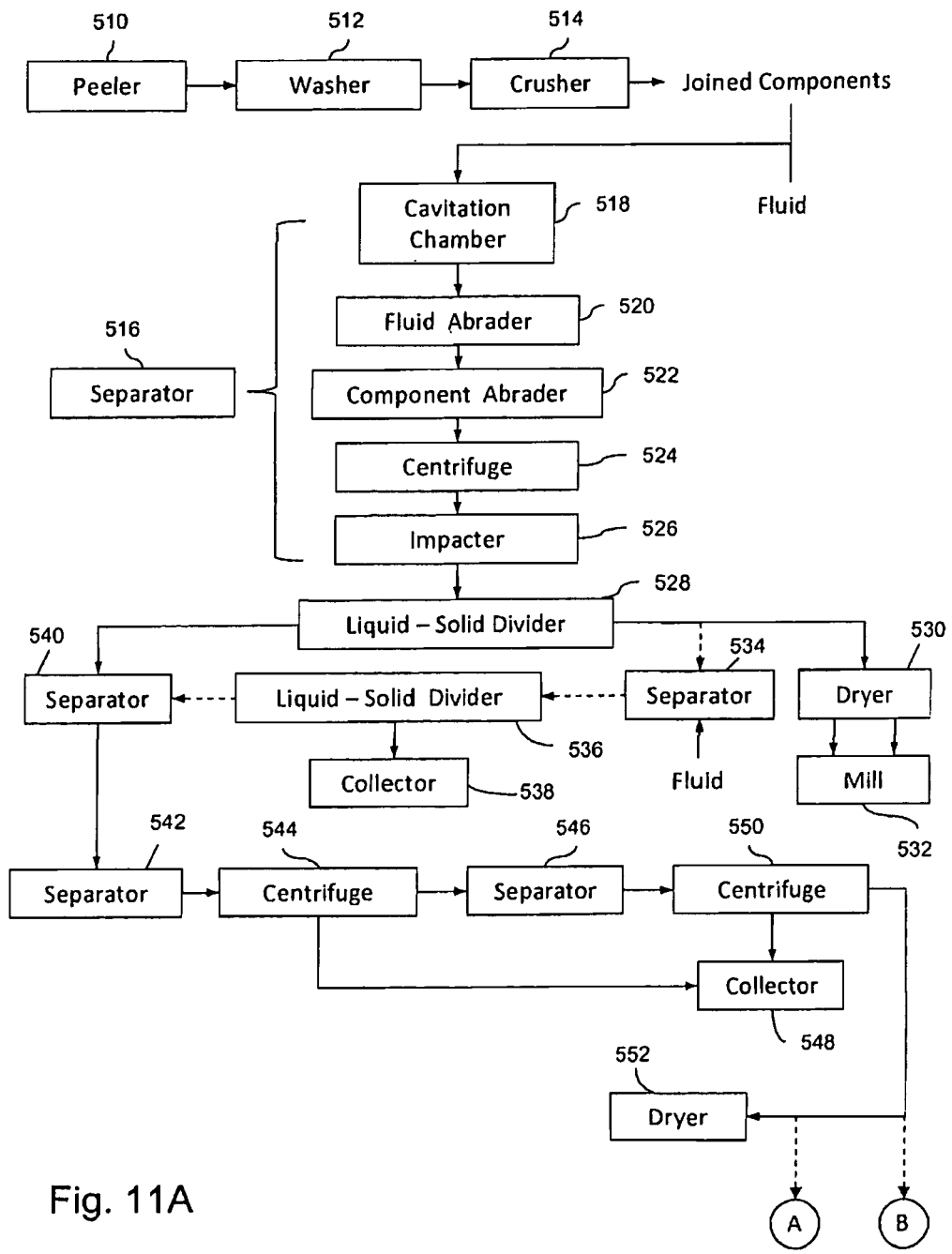
FIG. 11A is a flow diagram of a method of separation according to the present invention.
Figure 11B:
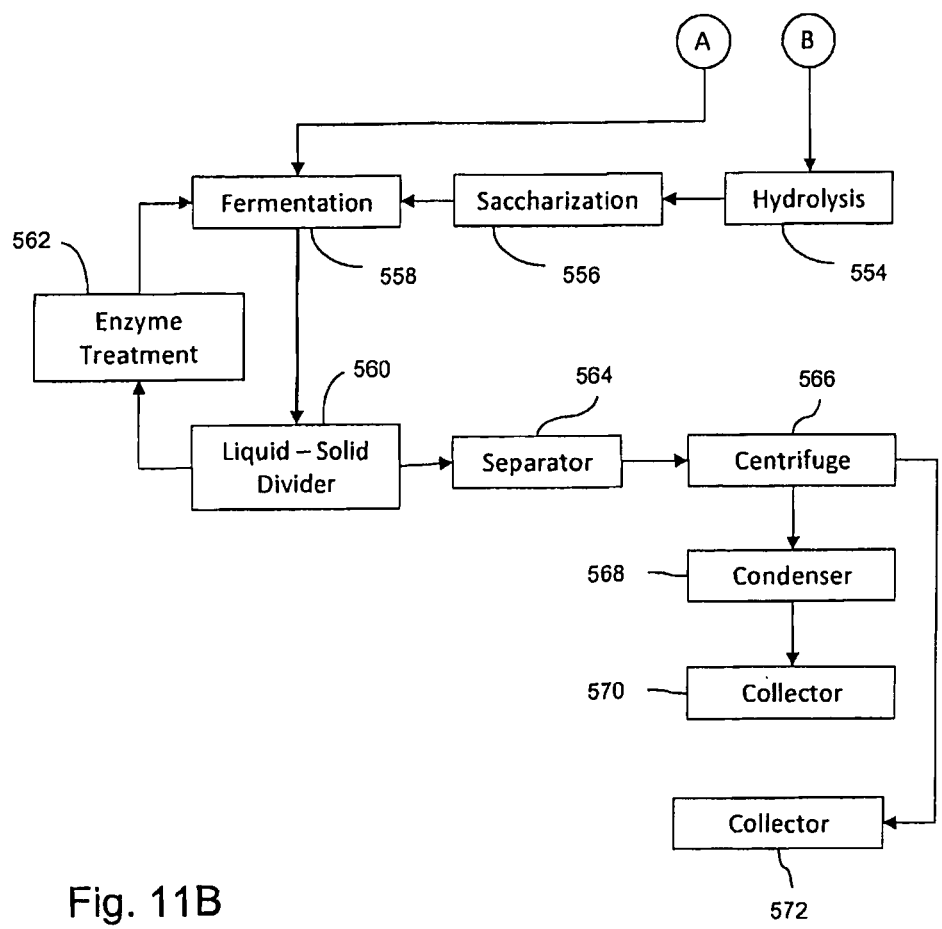
FIG. 11B is a continuation of the flow diagram of FIG. 11A.

FIGS. 11A and 11B show a method for separating joined components. If necessary, the joined components are peeled at 510, washed at 512 and/or crushed at 514 during the beginning of the separation process, as shown in FIG. 11A. The joined components are then placed in a fluid medium and sent to a first separator 516. First separator 516 has a cavitation chamber 518, a fluid abrader 520, a component abrader 522, a centrifuge 524 and an impacter 526. The separator may have a structure as any of the apparatuses 10, 110 and 210 described above, and it should be appreciated that the same structure may perform steps 518-526 simultaneously.

In the cavitation chamber 518, cavitation is induced in the fluid as described above in connection with apparatus 10 shown in FIGS. 1-3. The ultrasonic waves resulting from the creation and implosion of cavitation bubbles within the fluid is one factor in separating the joined components. The other steps in separator 516 are also factors in separating the joined components. Fluid abrader 520 induces abrasion between the fluid and joined components and component abrader 522 induces abrasion between the joined components to separate the components. Abrasion between the joined components may be abrasion between the individual components, or it may be abrasion between discrete units of joined components. Centrifuge 524 subjects the joined components to centrifugal force and impacter 526 subjects the joined components to impact forces to separate the components. After separation, the components are positioned throughout the fluid medium.

The separated components exit separator 516 and go to liquid-solid divider 528 which divides relatively large solid components from the fluid medium. Solid components of fine granulometry form a suspension with the fluid and are not divided from the fluid by liquid-solid divider 528. Liquid-solid divider 528 may be a sieve or any other suitable apparatus for dividing solids from liquid. The solid components divided from the fluid medium are dried by dryer 530 which also has the capability to further separate the solid components. The solid components are then ground in a mill 532 to a desired size. Alternatively, the solid components exiting liquid-solid divider 528 are placed in a fluid medium and sent to separator 534, where the same steps occur as in separator 516. Separator 534 further separates the solid components in the manner as described above with respect to separator 516. The fluid and separated solid components go to liquid-solid divider 536 where relatively large solid components are divided from the fluid and sent to a collector 538. Solid components of fine granulometry form a suspension with the fluid and are not divided from the fluid by liquid-solid divider 536. The suspensions of fluid and solid components of fine granulometry exiting liquid-solid dividers 528 and 536 combine at separator 540.

Separator 540 performs the same steps as separator 516 and further separates joined components within the fluid. The fluid and components exiting separator 540 flow into separator 542 which performs the same steps as separator 516. Separator 542 further separates the joined components within the fluid. The fluid and components exiting separator 542 flow into centrifuge 544, which may have a structure as the hydrocyclone described above in connection with FIG. 10. Centrifuge 544 subjects the fluid and components to a centrifugal force to divide the components based on density. Heavier components exiting centrifuge 544 go to separator 546, while lighter components exiting centrifuge 544 go to collector 548. After exiting separator 546, the heavier components enter centrifuge 550 which again divides the components based on density. Heavier components exiting centrifuge 550 go to a dryer 552, while lighter components go to collector 548. Either of the heavier or the lighter components may be further processed to achieve a desired end product.

If the resulting heavier components are starch or sugar, then instead of going to dryer 552, they may undergo an alternate process shown in FIG. 11B to convert the starch or sugar into ethanol. For ethanol production, starch exiting centrifuge 550, shown in FIG. 11A, follows path B to undergo hydrolysis, or liquefaction, at station 554, shown in FIG. 11B. Sugar exiting centrifuge 550, shown in FIG. 11A, follows path A to undergo fermentation at station 558, shown in FIG. 11B. For starch, at station 554 it is heated and joined with enzymes to promote hydrolysis. The hydrolyzed starch is then joined with enzymes and undergoes saccharization at station 556 where the hydrolyzed starch is converted into sugar syrup. The hydrolysis at station 554 and saccharization at station 556 may each be performed by any of the apparatuses 10, 110 and 210 shown in FIGS. 1-5, and according to the method of promoting interaction shown in FIG. 13 and described below in connection with FIG. 13.

The sugar syrup exiting station 556 is joined with yeast and undergoes fermentation at station 558 (the step where sugar exiting centrifuge 550 begins). Fermentation of the sugar syrup produces liquid ethanol. A heat exchanger (not shown) may be coupled with the apparatus performing fermentation step 558 for removing heat from the apparatus. After fermentation, the liquid ethanol goes to liquid-solid divider 560. Solids remaining in the liquid ethanol are divided from the ethanol and undergo enzyme treatment at step 562 to hydrolyze and saccharize the solids converting them to sugar syrup. This sugar then undergoes fermentation at station 558. Step 562 may be performed in a substantially similar manner as steps 554 and 556.

Liquid ethanol exiting liquid-solid divider 560 begins a distillation process at a separator 564, which has substantially the same configuration as separator 516. A heater (not shown) may be coupled with the separator 564 for heating the liquid. Preferably, the heater heats the liquid ethanol to approximately 80 degrees Celsius. The liquid ethanol may be heated before entering separator 564 by passing through a copper coil immersed in water heated by solar energy. Separator 564 induces cavitation within the liquid ethanol. The rapid creation and implosion of cavitation bubbles within the liquid ethanol converts it to ethanol vapor, however, some liquid may exit separator 564 with the ethanol vapor. The liquid remaining may be liquid ethanol and/or liquid added in a previous step that could not be converted into ethanol. The liquid and ethanol vapor exit separator 564 and go to centrifuge 566, which may have a structure similar to the hydrocyclone shown in FIG. 10. Centrifuge 566 subjects the liquid and ethanol vapor to a centrifugal force dividing the ethanol vapor from the liquid. Liquid exiting centrifuge 566 is collected by collector 572 where it is discarded or sent to undergo a second distillation process to recover any remaining ethanol within the liquid. The ethanol vapor exiting centrifuge 566 goes to a condenser 568 which condenses the vapor into a liquid. The liquid ethanol is collected by collector 570.

The joined components that are separated by the process shown in FIGS. 11A and 11B may be solids, liquids, gases or any combination of the three. For separating solids, the percent of solids in the fluid medium is preferably about 10-40% by volume. The separation process may be affected by varying the percent of solids placed within the fluid medium. A higher percentage of solids in the fluid medium results in increased abrasion between the solid components, while a lesser percentage of solids in the fluid medium results in decreased abrasion between the solid components. The components that are larger than the gaps between adjacent protrusions will impact the protrusions a number of times more than the components that are smaller than the gaps between adjacent protrusions, until the larger components fractionate and become smaller than the gaps. When the larger components fractionate into components that are smaller than the gaps between adjacent protrusions, the fractionated components can exit the apparatus through the gaps. The percent by volume of solids in the fluid medium may be varied as necessary for optimal separation of the type of components being separated. Further, the dimensions of the rotors and counter-rotors, including the gap size between adjacent protrusions, and the size and type of protrusions, may be varied for optimal separation.

Other external factors which may affect the separation process shown in FIGS. 11A and 11B include the pH level, viscosity and temperature of the fluid medium or components. As the pH level moves from neutral to acidity or alkalinity, the hydrogen potential permits greater atomic activity which may accelerate separation. The forces (cavitation, fluid abrasion, component abrasion, centrifugal and impact) generated within the separators promote the atomic activity by fostering contact between the fluid medium and joined components. An increase in viscosity of the fluid medium reduces the effects of cavitation within the fluid by restricting the formation, implosion and movement of cavitation bubbles. An increase in temperature increases the effects of cavitation within the fluid by reducing the attraction of the molecules of the liquid and thereby increasing the vapor pressure of the fluid medium. Cavitation bubbles form more frequently when the vapor pressure of the fluid medium is increased because less reduction in pressure is necessary to reduce the fluid pressure below the increased vapor pressure.

The method of separating shown in FIGS. 11A and 11B may be used to separate the joined components of a corn kernel, namely, the endosperm, pericarp and germ. Preferably, the corn bypasses peeler 510 and is washed in washer 512. After washing, the corn bypasses crusher 514 and is sent to separator 516. Separator 516 separates the endosperm, germ and pericarp by the method described above. The floury part of the endosperm has a fine granulometry and thus forms a suspension with the fluid after separation. The remainder of the endosperm, i.e., the grits, has a crystalline structure and is preferably comminuted by milling and digestion to become suspended in the fluid after the germ and pericarp are removed, as discussed in detail below in connection with the process shown in FIGS. 29A-D. Preferably, the mixture of fluid and corn kernels entering separator 516 is about 10 to 20% corn kernels by volume. Separator 516 preferably has a construction as apparatus 10 shown in FIGS. 1-3. For corn separation, the rotor preferably has one row of protrusions. The diameter of the row is preferably about 124 millimeters and the diameter of the protrusions about 9.5 millimeters. Preferably, the height of the protrusions is about 15 millimeters and the thickness of the rotor is about 10 millimeters. There is a distance of about 10 millimeters between protrusions. Preferably, the rotor rotates at a speed of between about 600 to 4500 revolutions per minute, and in a most preferred embodiment at a speed of either about 1100 or 1800 revolutions per minute. The process of separating the endosperm, germ, and pericarp occurs within about two minutes. Also, it is not necessary to steep the corn kernels in water or an acidic solution before separation as it is in conventional separation processes.

For separating corn according to the method shown in FIGS. 11A and 11B, separator 516 could be replaced by a plurality of separators coupled together each having a structure similar to apparatus 10. In this configuration each subsequent separator in the series has a gradually reduced distance between protrusions. There may be eight coupled separators replacing separator 516, where the distance between protrusions is gradually reduced from 10 millimeters to 7.5 millimeters.

Liquid-solid divider 528 divides the germ and pericarp from the fluid and endosperm suspension after separation of the endosperm, germ and pericarp. The germ and pericarp go to dryer 530, which is preferably a pneumatic type 60 degrees Celsius hot air drying system having the capability to divide the pericarp from the germ. The pericarp and germ may then be ground separately at mill 532 to meet market requirements. The fluid and endosperm suspension goes to separator 540. If ethanol production is desired, it is also within the scope of the invention for the endosperm suspension exiting liquid-solid divider 528 to bypass the starch/protein separation process described below and pass directly to the hydrolysis, saccharization, fermentation, and distillation steps shown in FIG. 11B.

Separator 540 induces cavitation within the fluid and endosperm suspension, abrasion between the fluid and endosperm, impacts between the endosperm and protrusions, and centrifugal force in order to separate starch and protein from the endosperm cells. Preferably, separator 540 comminutes the endosperm as discussed below in connection with the digestion reactors shown in FIGS. 29A-D so that sulfur dioxide within the sulfur towers described below can quickly interact with the endosperm molecules. Preferably, separator 540 has a structure similar to apparatus 10 except for having a rotor with two rows of protrusions. Separators 542 and 546 each separate starch and protein that is joined. Centrifuges 544 and 550 divide the separated starch and protein. The centrifuges are preferably centrifugal decanters, but may also be similar to or have the same structure as the hydrocyclone shown in FIG. 10. Centrifuges 544 and 550 subject the separated starch and protein to a centrifugal force dividing the starch and protein. The starch, which is heavier than the protein, travels around the interior wall of centrifuges 544 and 550 and exits at the bottom of the centrifuges with the fluid. The protein exits through the top of the centrifuges 544 and 550 and goes to collector 548.

After exiting centrifuge 550, the starch may either go to dryer 552, or it may be hydrolyzed, saccharized, fermented and distilled for producing ethanol according to the steps described above and shown in FIG. 11B. The starch is of higher quality than starch produced with conventional milling processes because the corn is not steeped for 35-50 hours in an acidic environment as in conventional processes. The endosperm slurry and starch produced in accordance with the process described herein typically yields more alcohol per unit weight than similar products produced in accordance with conventional milling processes.

The method of separating shown in FIG. 11A may also be used for producing corn atole. Corn is placed in water and sent through separator 516 which separates the germ, pericarp and endosperm. Liquid-solid divider 528 divides the germ and pericarp from the fluid and endosperm suspension. The germ and pericarp go to dryer 530 and mill 532. The endosperm is digested and dried producing atole powder. Atole produced according to conventional methods contains sulfur because the corn is steeped in a sulfur solution. The atole produced according to the method described herein does not contain sulfur because the corn is not steeped in a sulfur solution. Therefore, atole produced according to the present method is healthier and tastes better than atole produced according to conventional methods.

The method of separation shown in FIG. 11A may also be used as part of a corn nixtamalization process. After the corn kernels are separated into their components using the method of separation described herein, the different components of the kernels, i.e., the grits, fiber and pericarp, may be combined in different proportions than those occurring naturally in the corn kernels. Then, the combined components may be processed by a conventional extrusion process to produce nixtamalized corn flour. Thus, the separation process can be used to produce nixtamalized corn flour having a different proportion of fiber, grits, and pericarp than the natural proportion of those components in the corn. Further, the process of the present invention could produce nixtamalized corn flour in a few minutes versus approximately 2 to 4 hours for a conventional process.

Coffee berries may also be separated according to the method shown in FIG. 11A. The joined components of a coffee berry are the skin, pulp, mucilage, parchment and bean. Conventional processes for separating the components of a coffee berry require the steps of depulping the berry, fermenting the bean to loosen the mucilage, washing the bean to remove the mucilage, drying the bean, and shelling the bean to remove the parchment. It typically takes about 1 to 7 days to perform these steps. Separator 516 of the method shown in FIG. 11A separates the components of a coffee berry in only 7 to 10 seconds. The present method also produces higher quality coffee beans because they are neither subject to the crushing action of a depulping mill nor to a typical fermentation process. The present method for processing coffee costs about 30% less than conventional methods due to increased efficiency.

Preferably, for coffee separation the mixture of fluid to coffee berries is about 15 to 22% coffee berries by volume. Preferably, the first separator is an apparatus as shown in FIGS. 1-3 with a rotor as described below and a distance between protrusions about 50% greater than the longest coffee bean in order to ensure no beans are damaged. There are a variety of different rotors that are sufficient for coffee separation according to the method shown in FIG. 11A. One type of rotor has three rows of protrusions with each row having a respective diameter of 20 centimeters, 30 centimeters and 40 centimeters. The protrusions are cylindrical with a diameter of about 10 millimeters. The distance between the protrusions decreases from about 15 millimeters at the first row to about 10 millimeters at the third row. A second type of rotor has 19 cylindrical protrusions each having a diameter of about 0.375 inches. The protrusions are adjacent the peripheral edge of a rotor having a diameter of about 124 millimeters. There is a distance between protrusions of about 9 millimeters. A third type of rotor has 21 cylindrical protrusions each having a diameter of about 0.375 inches. The protrusions are adjacent the peripheral edge of a rotor having a diameter of about 124 millimeters. There is a distance between protrusions of about 7.5 millimeters. A fourth type of rotor has 20 protrusions with a C-shaped top profile, as shown in FIG. 6, each having a diameter of about 9.5 millimeters. The protrusions are adjacent the peripheral edge of a rotor having a diameter of about 124 millimeters. There is a distance between protrusions of about 7.5 millimeters. A fifth type of rotor has 14 protrusions with a C-shaped top profile, as shown in FIG. 6, each having a diameter of about 0.5 inches. The protrusions are adjacent the peripheral edge of a rotor having a diameter of about 124 millimeters. There is a distance between protrusions of about 16 millimeters. A sixth type of rotor has 20 conical protrusions each having a base diameter of about 12 millimeters and a crown diameter of about 4 millimeters. The protrusions are adjacent the peripheral edge of a rotor having a diameter of about 125 millimeters. A seventh type of rotor has 24 conical protrusions each having a base diameter of about 9.5 millimeters and a crown diameter of about 4 millimeters. The protrusions are adjacent the peripheral edge of a rotor having a diameter of about 124 millimeters.

After the beans, pulp, mucilage, pericarp and parchment of the coffee berries are separated by separator 516, the beans are divided from the pulp, mucilage, pericarp and parchment by a divider. The divider may be a sieve, or series of sieves designed to divide the various components based on size. The coffee beans are then dried, graded and packed for shipping. The pulp, mucilage, pericarp and parchment are sent to another separator preferably having a similar structure to apparatus 10 shown in FIGS. 1-3. The separated components then go to a divider which divides the pulp and mucilage from the parchment and pericarp. The pulp and mucilage may be fermented for production of ethanol as described above in connection with FIG. 11B, used to produce methane gas, or gums may be obtained from the mucilage. The parchment and pericarp preferably undergo an extraction process which extracts nutraceutic substances and/or fibers from the components.

The method shown in FIGS. 11A and 11B may also be used to separate the starch and cells of a cassava root. The cassava root is preferably peeled at peeler 510, washed at washer 512 and crushed at crusher 514 before being placed in water. The ratio of water and crushed cassava root is about 25 to 35% cassava root by volume. The cassava root is sent through separator 516 which preferably has a structure similar to apparatus 10 shown in FIGS. 1-3. After separator 516, starch separated from the solid cassava biomass forms a suspension with the water. The solid cassava biomass, water and starch go to liquid-solid divider 528 where the starch and water suspension is divided from the solid cassava biomass. The starch and water suspension goes to separator 540. The solid cassava biomass is placed in water and goes to separator 534 for further separation of starch and solid cassava biomass. Liquid-solid divider 536 divides the starch and water suspension exiting separator 534 from the solid cassava biomass. The solid cassava biomass goes to collector 538 and the starch and water suspension goes to separator 540 where it joins the starch and water suspension from divider 528. From separator 540, the process continues as described above with respect to separating corn. Preferably, the separators have rotors with protrusions having a diameter of about 9.5 millimeters and a distance between protrusions of about 10 millimeters. For separation of cassava root any of the separators may also have a dual-row rotor with a counter-rotor to improve breakdown of the root.

The method shown in FIGS. 11A and 11B may be used to separate sugar cane from sugar cane juice. The conventional process for recovering sugar cane juice from sugar cane comprises crushing or rolling the sugar cane to extract juice from the cane. Then, the cane is either discarded or recycled, where any cane juice still residing in the cane is lost. The method shown in FIGS. 11A and 11B retrieves about 9.5% sugar cane juice by weight from solid sugar cane that is discarded after a conventional cane juice extraction process.

According to the separation method of FIG. 11A, first, the sugar cane is crushed at crusher 514 and any sugar cane juice extracted during crushing is collected. Then, the crushed sugar cane is placed in water and sent through separator 516, which may have a structure similar to apparatus 10 shown in FIGS. 1-3. Preferably, the mixture of water and sugar cane is about 25 to 35% sugar cane by volume. Separator 516 separates the sugar cane juice from the sugar cane via the factors described above. Liquid-solid divider 528 divides the solid sugar cane from the water and cane juice. The solid sugar cane is again placed in water and sent through separator 534 which further separates sugar cane juice from the sugar cane. Liquid-solid divider 536 divides the sugar cane juice and sugar cane exiting separator 534. The solid sugar cane goes to collector 538 where it may be used as aggregate or in the production of paper. The sugar cane juice may be processed into crystalline sugar, or it may be fermented and distilled to produce ethanol as described above with respect to steps 558-572. Sugar beet juice may be separated from a sugar beet in the same manner as described above for separating sugar cane juice from sugar cane.

The method shown in FIG. 11A may also be used for separating gaseous impurities from liquids. For instance, the method may be used for separating sulfur dioxide, or other gaseous impurities, from liquid fuel. Sulfur-dioxide is a compound present in fuel that is released into the atmosphere upon combustion and is harmful to both health and environment. For separating fuel and sulfur dioxide according to the method shown in FIG. 11A, fuel containing sulfur dioxide is sent directly to a separator coupled with a centrifuge such as 542 and 544. Preferably, apparatus 410 as shown in FIG. 10 is used for separation of the sulfur dioxide and fuel. The separator induces cavitation within the liquid fuel. Cavitation enhances the formation of sulfur dioxide gas bubbles within the fuel. The centrifuge subjects the fuel to centrifugal force dividing the sulfur dioxide gas from the liquid fuel. Preferably, the sulfur dioxide gas exits through the top of the centrifuge and the purified fuel exits through the bottom of the centrifuge. Both the gas and the fuel may be collected in a collector.

The method shown in FIG. 11A may also be used to separate soil and dust from grain. For separation, grain covered in soil or dust is placed in water and sent through separator 516. The separator separates the grain and soil or dust. Liquid-solid divider 528 divides the clean grain from the soil or dust, which remain suspended in the water. Liquid-solid divider 528 may be a sieve. The clean grain is dried in dryer 530 and processed as desired.

The method shown in FIG. 11A may also be used for separating any components of vegetable or animal tissue. The vegetable or animal tissue is processed and selected, placed in water and sent through separator 516 for separation of the tissue components. The tissue components are then preferably divided by any method, washed, dried and packaged.

Soybeans may also be separated according to the method shown in FIG. 11A. The soybean separation method described herein greatly reduces the number of steps and equipment required by traditional methods. The joined components of soybeans are the shell, germ and endosperm. The soybeans are placed in water and sent through separator 516. Separator 516 separates the shell, germ and endosperm. Liquid-solid divider 528 may be used to divide the shell, germ and endosperm. Liquid-solid divider 528 may be a sieve or series of sieves sized to divide the components. The method may also be used to separate the joined components of other beans, grains such as sorghum, pineapple juice from pineapple fibers and starch from potatoes.

Figure 12:
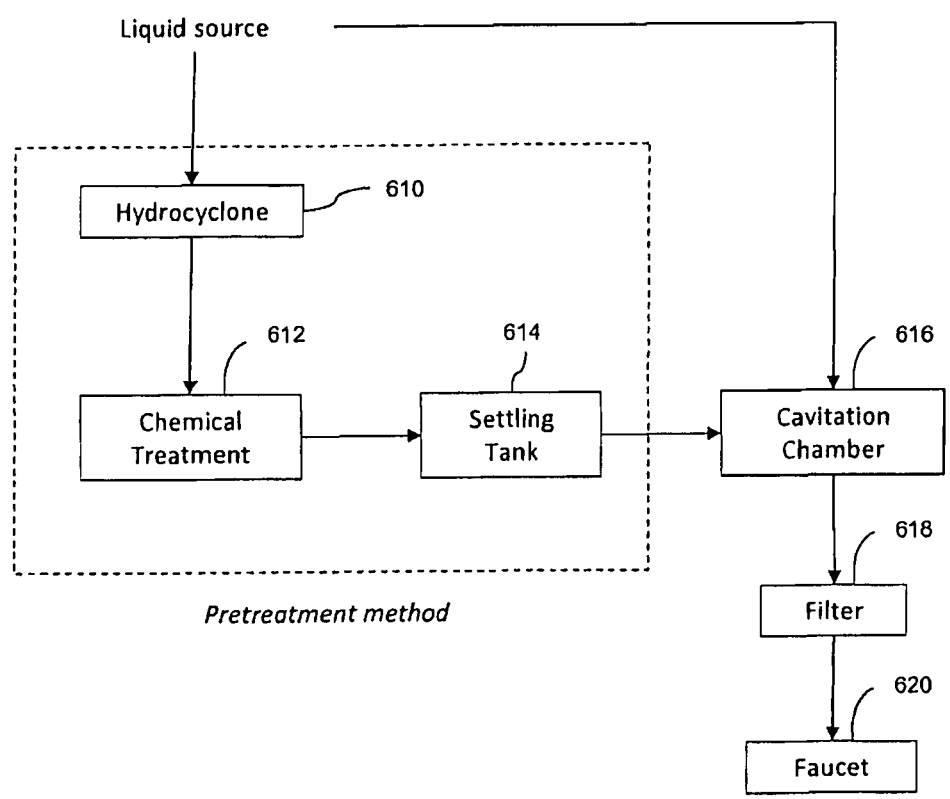
FIG. 12 is a flow diagram of a method of purification according to the present invention.

FIG. 12 shows a method for purifying liquid according to the present invention. If there are solids suspended in the liquid, the liquid preferably undergoes the pretreatment method of steps 610-614. If there are no solids suspended in the liquid, then the liquid may go directly to cavitation chamber 616. According to the pretreatment method, the liquid goes to a hydrocyclone 610 which helps to divide the liquid from the solids as discussed above in connection with the apparatus shown in FIG. 10. Next, the liquid undergoes chemical treatment 612, which preferably comprises adding coagulation chemicals which bond to sediment in the liquid and promote settling of the sediment. Settling tank 614 holds the liquid for an amount of time sufficient to allow the chemicals and sediment to settle at the bottom of the tank. The liquid in settling tank 614 then goes to cavitation chamber 616 where cavitation is induced within the liquid to kill undesirable organisms in the liquid. The undesirable organisms are killed by the rapid creation and implosion of the cavitation bubbles formed within the liquid. Cavitation chamber 616 may have a structure similar to any of the apparatuses 10, 110 and 210 described in connection with FIGS. 1-5. The cavitation may kill the organisms by cellular lysis. If the liquid to be purified is water, the cavitation and high temperature generated by the cavitation preferably promote ozonization of the water. The ozone kills undesirable organisms within the liquid. After undesirable organisms within the liquid are killed, the liquid is filtered at filter 618 removing any fine particulate remaining in the liquid before the liquid exits faucet 620.

Preferably, the cavitation chamber of the process shown in FIG. 12 has a structure like any of the apparatuses shown in FIGS. 1-5. Preferably, an apparatus used in the process of FIG. 12 has protrusions with a C-shaped top profile, as shown in FIG. 6, for maximizing cavitation within the liquid. An apparatus as shown in FIGS. 1-5 may be installed within a home or office to purify water entering the building from a public water line. Preferably, an apparatus installed for home or office water purification will have an inlet less than 0.5 inches and an outlet around 0.75 inches. An apparatus as shown in FIGS. 1-5 may also be installed within a water distribution line for purifying the water therein. The liquid that is purified using the method shown in FIG. 12 may be water, juice or any other liquid needing purification. For instance, this purification process may be used instead of or in addition to pasteurization to purify juice or milk. The purification process described herein is advantageous because the liquid is not heated and therefore the flavor of the liquid does not change. The purification process shown in FIG. 12 may also be used to purify wastewater.

The purification method of FIG. 12 may be used to purify liquid used for heat transfer. Undesirable organisms may flourish in water or other liquids used for heat transfer. It is desirable to kill these undesirable organisms to prevent sickness among individuals that may come into contact with the liquid. When liquid is used for heating purposes, a cavitation chamber and centrifuge may receive liquid from a heat exchanger, purify the liquid, then send the liquid to a boiler. The liquid then goes from the boiler to the heat exchanger and back to the cavitation chamber. When liquid is used for cooling purposes, a cavitation chamber may receive liquid from a heat exchanger, purify the liquid, then send the liquid to a cooling tower. The liquid then goes from the cooling tower to the heat exchanger and back to the cavitation chamber. The liquid purification may increase the efficiency of the heat transfer process by raising the specific heat capacity of the liquid.

Figure 13:
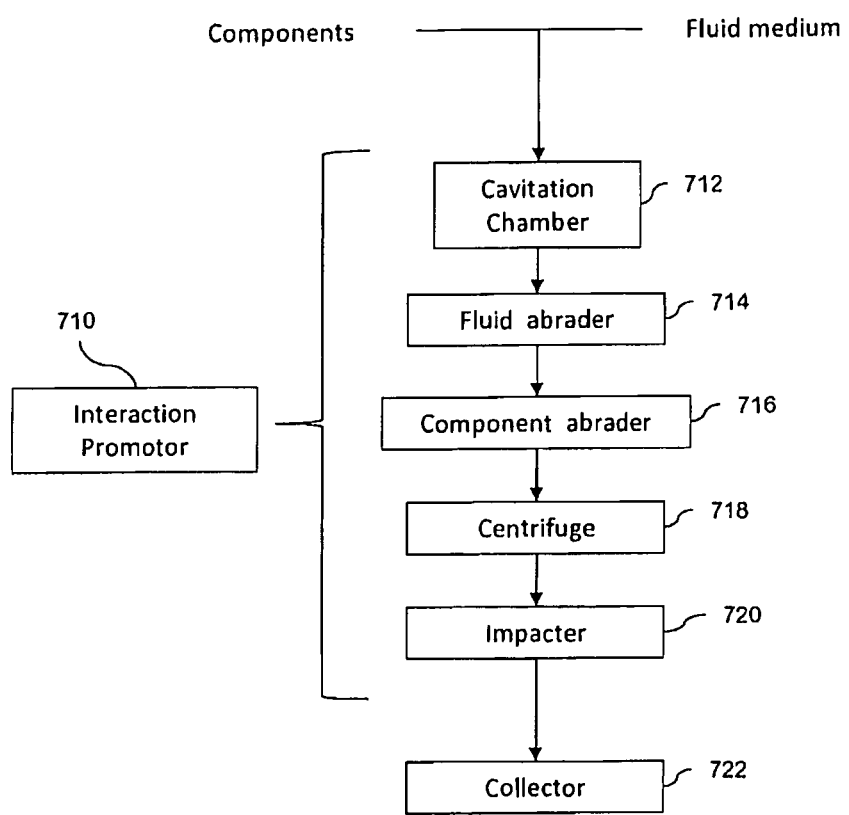
FIG. 13 is a flow diagram of a method of promoting interaction according to the present invention.

FIG. 13 shows a method of promoting interaction between two or more components in accordance with the present invention. The components are placed in a fluid medium and sent to an interaction promoter 710. Interaction promoter 710 has a cavitation chamber 712, a fluid abrader 714, a component abrader 716, a centrifuge 718 and an impacter 720. The interaction promoter may have a structure as any of the apparatuses 10, 110 and 210 described above in connection with FIGS. 1-5, and it should be appreciated that a single structure may simultaneously perform steps 712-720. Cavitation chamber 712 induces cavitation in the fluid for promoting interaction between the components. Fluid abrader 714 induces abrasion between the fluid and components and component abrader 716 induces abrasion between the components for promoting interaction between the components. Centrifuge 718 subjects the components to centrifugal force promoting interaction between the components, and impacter 720 subjects the components to an impact force to promote interaction between the components. Upon exiting interaction promoter 710, the interacted components are collected in a collector 722. The components which interact may be solid, liquid, gas, or any combination of the three.

The method of FIG. 13 may be used to promote any chemical or physical reaction, such as a hydrolysis reaction. For instance, the method may be used to promote the interaction of enzymes and starch for the purpose of hydrolyzing the starch. For example, the method may be used for processing biomass to obtain cellulosic ethanol. The starch and enzymes are placed in a fluid medium and sent through interaction promoter 710. The cavitation, abrasion, and other forces generated within the interaction promoter promote the interaction of the starch and enzymes resulting in the hydrolyzation of the starch. The method of FIG. 13 may further be used to promote saccharization of the hydrolyzed starch for creating a sugar syrup. The hydrolyzed starch and enzymes are placed in a fluid medium and sent through interaction promoter 710 which promotes the interaction of the enzymes and hydrolyzed starch. The cavitation, abrasion, and other forces generated within the interaction promoter promote the interaction of the hydrolyzed starch and enzymes to create a sugar syrup. The sugar syrup is then collected in collector 722.

It is also possible to emulsify and homogenize substances in accordance with the method for promoting interaction shown in FIG. 13. For example, the method may be used to produce banana puree from bananas, coconut crème from coconuts and meat broth from meat. The method may be used to emulsify fruit juices, ice cream, sauces, pharmaceutical pastes, chemical pastes and meat for sausage. The method may be used to promote the interaction of milk, fruit juices or fruit pulp with additional products before packaging. The method may also be used to accelerate a chemical or physical reaction occurring as a result of the interaction of two or more components. For instance, the method may be used to speed up the conversion of wood into pulp where the components for interaction comprise wood and one or more chemicals.

Figure 14:
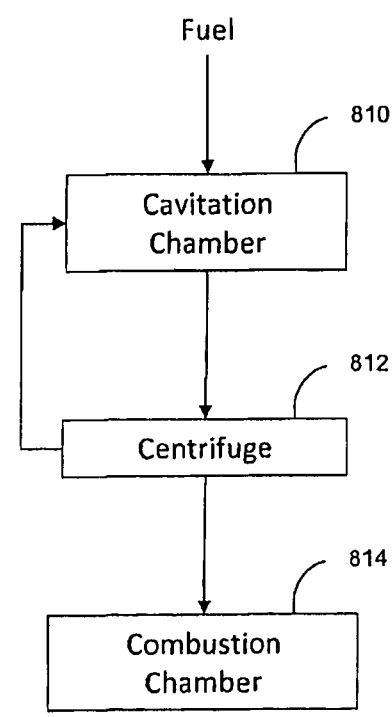
FIG. 14 is a flow diagram of a method of improving combustion according to the present invention.

FIG. 14 shows a method for improving the combustion of liquid fuel by vaporizing the liquid fuel. Vaporizing liquid fuel improves combustion because the fuel to air ratio is more evenly distributed throughout a combustion chamber 814. To vaporize fuel according to the present method, the fuel is sent through a cavitation chamber 810 where cavitation is induced in the fuel. The rapid creation and implosion of cavitation bubbles within the fuel vaporizes the fuel. After exiting the cavitation chamber 810 some liquid fuel may remain, therefore a centrifuge 812 subjects the vaporized and liquid fuel combination to centrifugal force dividing the vaporized fuel from the liquid fuel. Centrifuge 812 may have a similar structure as the hydrocyclone shown in FIG. 10. The vaporized fuel is mixed with oxygen and then combusted in a combustion chamber 814 and the liquid fuel is recycled back to cavitation chamber 810. Any apparatus shown in FIGS. 1-10 may be used to improve the combustion of liquid fuel according to the method shown in FIG. 14.

Method and System for Processing Biomass

A method and system for processing biomass is described herein with reference to FIGS. 15-29D. FIGS. 15-28B show apparatus that are used in the method for processing biomass and FIGS. 29A-D show a flow chart for the biomass processing method. The biomass processing method and system may be used to process any type of biomass including, but not limited to, grains such as corn, sorghum, and oats, beans such as soybeans and coffee berries, cassava root, sugar cane, sugar beet, and algae. The process and system can be used as steps in the production or refinement of any type of material derived from biomass, such as oil, fiber, starch, protein, and sugars. The process is preferably used for processing any type of starch bearing grain to obtain relatively pure output streams of the grain's components, which typically includes oil, fiber, starch, protein, and sugars.

Most preferably, the process is used to separate the endosperm, pericarp, and germ of corn kernels into a stream of endosperm slurry and a stream of pericarp and germ. The process then separates the starch and protein contained within the endosperm slurry. Once the molecules of starch and protein are separated, conventional equipment and processes may be used to divide and filter the separated starch and protein contained within the endosperm slurry into separate streams, as well as to filter any endosperm fiber contained within the slurry into a separate stream. Conventional equipment may also be used to divide the pericarp and germ stream into separate streams of pericarp and germ, as well as to process the pericarp and germ into desired end products. The process may also be used to process sorghum kernels in a similar manner as corn kernels.

The process and system described herein are advantageous over conventional biomass processing systems and methods because the process and system of the present invention produce higher quality products in less time. For example, with the process and system of the present application, it takes between approximately 5 minutes to 2 hours to separate the pericarp, germ, and endosperm of corn kernels into an endosperm stream and a pericarp and germ stream, as well as to separate starch and protein molecules in the endosperm stream. Further, the process and system of the present application, when used for corn processing, produces higher quality products than conventional corn processing methods. It is believed that the process and system of the present application produces higher quality products because it does not require steeping corn kernels for between approximately 35 to 50 hours in sulfur dioxide and water, as is done in conventional corn processing methods. It is believed that steeping corn for 35 to 50 hours in sulfur dioxide degrades the quality of the pericarp fiber, oil and starch produced.

FIGS. 15-27 show a variety of alternative embodiments of rotors, which can be used with any of the apparatus 10, 110, and 210 (FIGS. 1-5) in place of rotors 18, 118, and 218, respectively, and a variety of alternative embodiments of housing end wall configurations that can be used with apparatus 110 (FIG. 4) in place of end wall 114 and the protrusions 112 extending therefrom. It is also within the scope of the present invention to incorporate the housing end wall configurations that are shown in FIGS. 16A, 16B, 21, 23, 25, and 27 into a counter-rotor such as the counter-rotor 214 that is shown in FIG. 5. While preferable combinations of rotors and housing end wall configurations for use with the method and system of the present invention are described in detail below, any combination of rotors and end wall configurations in an apparatus 10, 110, or 210 are within the scope of the present invention.

Figure 15:
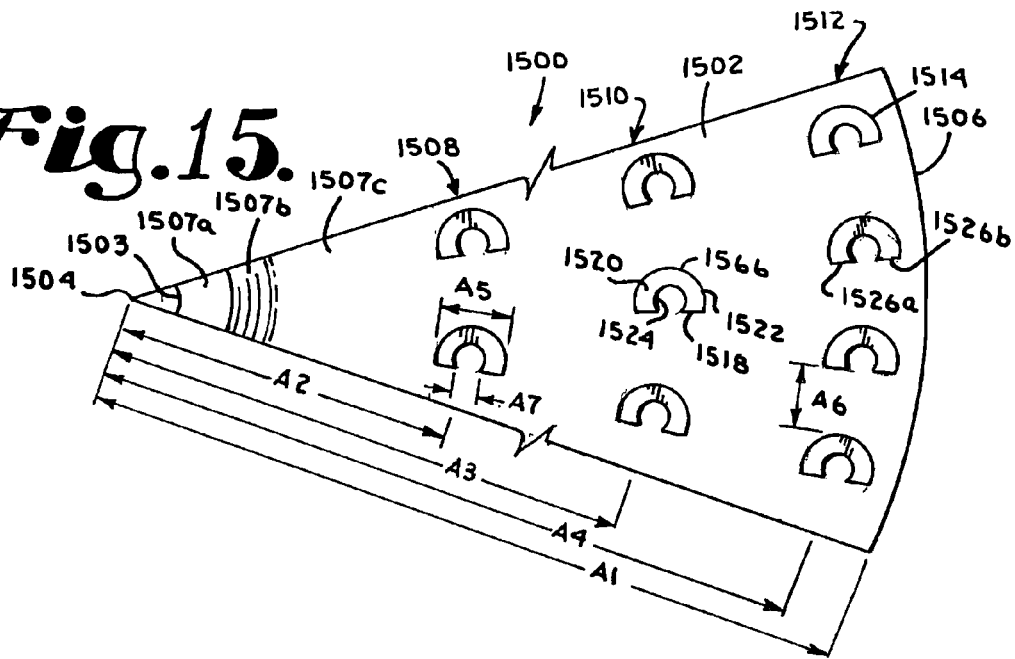
FIG. 15 is a front elevational view of a rotor having C-shaped protrusions.

FIG. 15 shows a portion of a rotor 1500 having a front surface 1502 that faces the end wall 24 when used with apparatus 10 of FIG. 1, the end wall 114 when used with the apparatus 110 of FIG. 4, or the counter-rotor 214 when used with the apparatus 210 of FIG. 5. Rotor 1500 is circular and has an opening 1503 with a center 1504, and an outer peripheral edge 1506. Opening 1503 is configured to receive a shaft like shaft 16 in FIG. 1 for mounting and rotating the rotor within an apparatus. Front surface 1502 comprises a raised flat surface 1507a surrounding opening 1503, an angled surface 1507b adjacent surface 1507a, and a flat surface 1507c positioned below surface 1507a and between surfaces 1507b and edge 1506. The portion of rotor 1500 not shown in FIG. 15 has the same configuration and pattern of protrusions as those on the portion of rotor 1500 shown in FIG. 15.

There are first, second, and third rows 1508, 1510, and 1512 of protrusions extending outward from front surface 1502. One of the protrusions is labeled as 1514. Each of the protrusions 1514 has a generally C-shaped top profile or cross-section, like the protrusions 310 in FIG. 6, with a leading edge 1516 and a trailing edge 1518. The rotor 1500 preferably rotates counter-clockwise in the direction of the leading edge 1516 such that when the rotor rotates, fluid flows around the protrusions 1514 from the leading edge 1516 toward the trailing edge 1518.

Each protrusion 1514 has a base that is joined to front surface 1502 and a top surface 1520. The height of each protrusion is defined as the distance from the base of the protrusion to the top surface 1520. The protrusion has an outer surface 1522, which incorporates leading edge 1516, an inner surface 1524 that is concentric with outer surface 1522, and a pair of rear surfaces 1526a and 1526b each extending between outer surface 1522 and inner surface 1524 and each forming the trailing edge 1518 of the protrusion. Each of surfaces 1522, 1524, and 1526a,b extends from the front surface 1502 of rotor 1500 to the top surface 1520 of the protrusion 1514. It is believed that this design when rotated in a counter-clockwise direction generates significant cavitation near trailing edge 1518 due to a reduction in pressure in that region as the rotor rotates.

As shown in FIG. 15, rotor 1500 has a radius A1 measured from the center 1504 to the outer peripheral edge 1506. The first row 1508 of protrusions has a radius A2, the second row 1510 of protrusions has a radius A3, and the third row 1512 of protrusions has a radius A4. Radiuses A2, A3, and A4 are measured from the center 1504 to the center of the protrusions 1514 in rows 1508, 1510, and 1512, respectively. Each of the protrusions 1514 has a diameter A5. The distance between adjacent protrusions is A6. The distance A6 may vary between protrusions in the same row and/or between rows 1508, 1510, and 1512.

Like FIG. 15, FIGS. 17A, 17B, 18A, 18B, 19, 20A, 20B, 22, 24, and 26 also show the front surface of rotors that face the end walls 24, 114 or counter-rotor 214 of apparatus 10, 110, and 210, respectively. Similarly, each of the rotors shown in FIGS. 17A-20B, 22, 24, and 26 is circular and the portions of the rotors not shown in the drawings have the same configuration and pattern of protrusions as the portions of the rotors shown in the drawings.

Figure 16A:
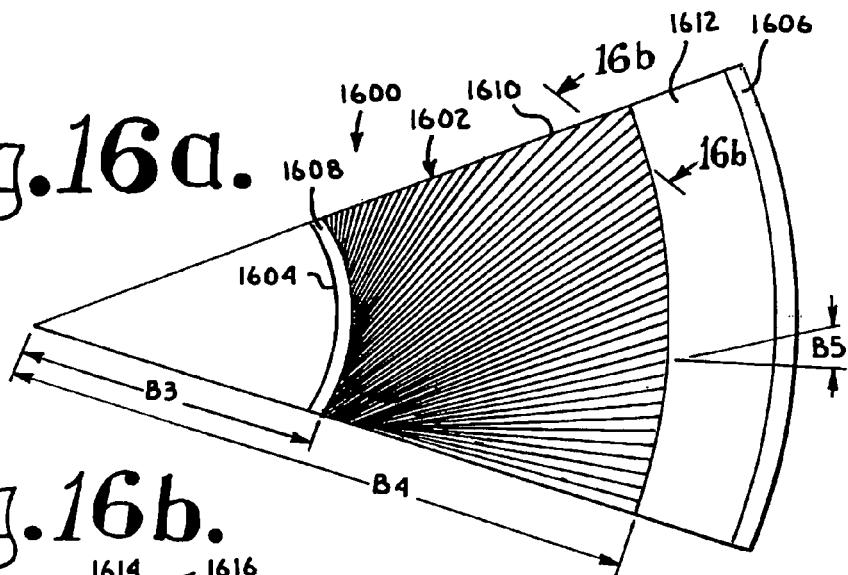
FIG. 16A is a front elevational view of a housing end wall configuration having grooves.
Figure 16B:
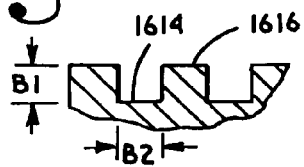
FIG. 16B is a cross-sectional view taken through the line 16B-16B in FIG. 16A.

FIGS. 16A and 16B show a portion of a housing end wall configuration that can be used with apparatus 110 (FIG. 4) in place of end wall 114. As described above, this end wall, and any of the end walls described herein, could also be used in apparatus 210 (FIG. 5) in place of counter-rotor 214. As shown in FIG. 16A, a housing 1600 has an end wall 1602 and an opening 1604 for allowing fluid and biomass to enter the housing. The end wall 1602 of the housing 1600 can be substituted for the end wall 114 shown in FIG. 4. The remainder of housing 1600 is substantially similar to housing 116 of FIG. 4. The end wall 1602 extends from opening 1604 to a side wall 1606 of the housing, which is similar to, for example, side wall 28 of the housing shown in FIG. 1. The end wall 1602 has a flat section 1608 adjacent opening 1604, a grooved section 1610 adjacent section 1608, and a flat section 1612 between section 1610 and wall 1606.

As shown in FIGS. 16A and 16B, the grooved section 1610 has alternating grooves 1614 and raised sections 1616. The raised sections 1616 are coplanar with sections 1608 and 1612. The grooves 1614 are rectangular shaped; however, any shape of groove such as triangular is within the scope of the invention. The grooves 1614 have a depth B1, which is the distance from an upper surface of the raised sections 1616 to a lower surface of the grooves 1614, and a width B2. The width B2 of each groove 1614 may be variable such that the width slightly increases along the groove's length from section 1608 to section 1612. Referring to FIG. 16A, the grooved section 1610 has an inner radius B3 and an outer radius B4, which are measured from the center of opening 1604. The grooves 1614 are positioned at an angle B5 with respect to an imaginary radial line that is perpendicular with side wall 1606 and that passes through the center of opening 1604.

FIG. 17A shows an alternative embodiment of rotor 1700 having a front surface 1702, an opening 1704, which is configured to receive a shaft, and an outer peripheral edge 1706. Opening 1704 has a center 1708. Front surface 1702 comprises a raised flat surface 1709a surrounding opening 1704, an angled surface 1709b adjacent surface 1709a, and a flat surface 1709c positioned below surface 1709a and between surfaces 1709b and edge 1706. There are first, second, and third rows 1710, 1712, and 1714 of protrusions extending outward from front surface 1702. One of the protrusions is labeled as 1716. Each of the protrusions 1716 is cylindrical with a base that is joined with front surface 1702, a side wall 1718 extending outward from surface 1702, and a top surface 1720. The height of each protrusion 1716 is defined as the distance from the base of the protrusion to the top surface 1720.

Rotor 1700 has a radius C1 measured from the center 1708 to the outer peripheral edge 1706. The first row 1710 of protrusions has a radius C2, the second row 1712 of protrusions a radius C3, and the third row 1714 of protrusions a radius C4. Radiuses C2, C3, and C4 are measured from the center 1708 to the center of the protrusions 1716 in rows 1710, 1712, and 1714, respectively. Each of the protrusions has a diameter C5. The distance between adjacent protrusions is C6. The distance C6 may vary between protrusions in the same row and/or between rows 1710, 1712, and 1714.

FIG. 17B shows an alternative embodiment of rotor 1750, which is substantially similar to rotor 1700. Thus, only the differences between rotors 1700 and 1750 are discussed herein. Rotor 1750 has first, second, and third rows 1752, 1754, and 1756 of protrusions. One of the protrusions is labeled as 1758. Rotor 1750 has a front surface 1760 having openings 1762 therein that are positioned between adjacent protrusions 1758 of the second and third rows 1754 and 1756.

FIGS. 18A and 18B show another embodiment of rotor 1800 having a front surface 1802, an opening 1804, which is configured to receive a shaft, and an outer peripheral edge 1806. Opening 1804 has a center 1808. Front surface 1802 comprises a raised flat surface 1809a surrounding opening 1804, an angled surface 1809b adjacent surface 1809a, and a flat surface 1809c positioned below surface 1809a and between surfaces 1809b and edge 1806. There are first, second, and third rows 1810, 1812, and 1814 of protrusions extending outward from front surface 1802. One of the protrusions is labeled as 1816. Each of the protrusions 1816 is cylindrical with a base that is joined with front surface 1802, a side wall 1818 extending outward from surface 1802, and a top surface 1820. The height of each protrusion 1816 is defined as the distance from the base of the protrusion to the top surface 1820.

There is a distance D1 between adjacent protrusions 1816 in first row 1810. The side walls 1818 of adjacent protrusions 1816 in second and third rows 1812 and 1814 abut so that there is no gap between the protrusions in those rows. Further, as best shown in FIG. 18B, the protrusions 1816 in second and third rows 1812 and 1814 have alternating heights. One set of protrusions 1822 has a height D2 that is less than the height D3 of an alternating set of protrusions 1824.

Rotor 1800 has a radius D4 measured from the center 1808 to the outer peripheral edge 1806. The first row 1810 of protrusions has a radius D5, the second row 1812 of protrusions a radius D6, and the third row 1814 of protrusions a radius D7. Radiuses D5, D6, and D7 are measured from the center 1808 to the center of the protrusions 1816 in rows 1810, 1812, and 1814, respectively. Each of the protrusions has a diameter D8.

FIG. 19 shows a closed rotor 1900 having a central hub 1902 with an opening that is configured to receive a threaded stud 1904 that is coupled with a shaft and motor like shaft 16 and motor 22 shown in FIG. 3. A nut 1906 secures rotor 1900 to stud 1904. Although not shown in FIGS. 1-5, 15, 17A-20B, 22, 24, and 26, the rotors shown in those embodiments are also preferably joined with a shaft and motor in a similar manner as that shown in FIG. 19.

Rotor 1900 has opposed front and rear circular plates 1908 and 1910 and a plurality of curved vanes 1912 positioned therebetween. The front plate 1908 has an opening 1914 for allowing fluid and biomass to pass therethrough into the void space between plates 1908 and 1910 where vanes 1912 can act on the fluid and biomass. When installed within an apparatus such as apparatus 10 of FIG. 1, fluid enters the rotor opening 1914 through the inlet 32 where the vanes 1912 increase the pressure and/or velocity of the fluid. The fluid exits the rotor and apparatus through outlet 34 (FIG. 1). Each of the plates 1908 and 1910 of rotor 1900 has a diameter of preferably approximately 300 millimeters.

FIGS. 20A and 20B show an alternative embodiment of rotor 2000. Rotor 2000 has a front surface 2002, an opening 2004, which is configured to receive a shaft, and an outer peripheral edge 2006. Opening 2004 has a center 2008. The front surface 2002 comprises a raised flat surface 2010a surrounding opening 2004a, an angled surface 2010b surrounding surface 2010a, a flat surface 2010c positioned below surface 2010a and surrounding surface 2010b, an angled surface 2010d surrounding surface 2010c, a flat surface 2010e positioned below surface 2010c and surrounding surface 2010d, and a grooved section 2012.

The grooved section 2012 has a plurality of grooves of alternating lengths extending from the flat section 2010e to the edge 2006. A first set of grooves 2014 has a first length that is shorter than the length of a second set of grooves 2016. The lengths of the grooves 2014 and 2016 are defined as the distance of the grooves from the edge 2006 to the end of the grooves near section 2010e. Sets of grooves 2014 and 2016 alternate around the rotor 2000. The grooves 2014 and 2016 are triangular shaped, as shown in FIG. 20B each having opposite walls 2017a and 2017b that join at a bottom edge of the groove 2017c. However, any shape of groove such as rectangular is within the scope of the invention. Raised sections 2018 are positioned between each pair of adjacent grooves 2014 and 2016. The raised sections 2018 have an upper surface 2019 (FIG. 20B) that is coplanar with section 2010e.

Referring to FIGS. 20A and 20B, at the outer peripheral edge 2006 of the rotor, a plurality of vanes 2020 are milled or drilled into the raised sections 2018. Vanes 2020 assist in moving liquid and fluid through an apparatus containing rotor 2000 and in creating more pressure at the output of the apparatus. The vanes 2020 consist of an outer surface 2022, which forms a portion of edge 2006, and a curved surface 2024, which extends from outer surface 2022 to the bottom edge 2017c of one of the grooves 2014 and 2016. A plurality of vanes 2028 also extend outward from the edge 2006 of the rotor. Preferably, there are approximately eight or twelve vanes extending outward from the edge 2006 of the rotor. The eight or twelve vanes are preferably equally spaced circumferentially around the rotor. The structure of vane 2028 improves the rotor's ability to pump incoming fluid out of the apparatus that the rotor 2000 is installed within.

Like the grooves in FIG. 16, grooves 2014 and 2016 have a depth, which is the distance from upper surface 2019 to bottom surface 2026, and a width, which is the distance across a groove. The widths of the grooves may be variable between sets of groove's 2014 and 2016, and/or within a set of grooves 2014 and 2016. Further, the width of any single groove may be variable such that it increases or decreases from section 2010e to edge 2006. The grooved section has an inner radius E1, as measured from center 2008, and the entire rotor has a radius E2. The grooves 2014 and 2016 are positioned at an angle E3 with respect to an imaginary radial line that is perpendicular with edge 2006 and that passes through center 2008. The distance between two grooves in the second set 2016 of longer grooves is E4. Vane 2028 has a length E5, a width E6, and a height that is approximately the same as the thickness of the rotor. Vanes 2020 have a height E7 and a width E8, as shown in FIG. 20B.

FIG. 21 shows a portion of a housing end wall configuration that can be used with apparatus 110 (FIG. 4) in place of end wall 114. As shown in FIG. 21, a housing 2100 has an end wall 2102 and an opening 2104 for allowing fluid and biomass to enter the housing. The end wall 2102 of the housing 2100 can be substituted for the end wall 114 shown in FIG. 4. The end wall 2102 extends from opening 2104 to a side wall 2106 of the housing, which is similar to, for example, side wall 28 of the housing shown in FIG. 1. The end wall 2102 has a flat section 2108 adjacent side wall 2106, a grooved section 2110 adjacent section 2108, and an angled surface 2112 that extends down from grooved section 2110 to a flat surface 2114 adjacent opening 2104.

In the grooved section 2110, there are a plurality of grooves of alternating lengths extending from section 2112 to section 2108. A first set of grooves 2116 has a first length that is shorter than the length of a second set of grooves 2118. The lengths of the grooves 2116 and 2118 are defined as the distance of the grooves between sections 2108 and 2112. Sets of grooves 2116 and 2118 alternate around the rotor 2100. Raised sections 2120 are positioned between each pair of adjacent grooves 2116 and 2118. The raised sections 2120 have an upper surface that is coplanar with section 2108. The grooves 2116 and 2118 are triangular shaped like the grooves on the rotor in FIGS. 20A and B; however, any shape of groove such as rectangular is within the scope of the invention.

Like the grooves in FIG. 16, grooves 2116 and 2118 have a depth, which is the distance from the upper surface of the raised sections to the bottom surfaces of the grooves, and a width, which is the distance across a groove. The widths of the grooves may be variable between sets of grooves 2116 and 2118, and/or within a set of grooves 2116 and 2118. Further, the width of any single groove may be variable such that it increases or decreases along the length of the groove between sections 2108 and 2112. The grooved section has an inner radius F1 and an outer radius F2, which are measured from the center of opening 2104. The grooves 2116 and 2118 are positioned at an angle F3 with respect to an imaginary radial line that is perpendicular with wall 2106 and that passes through the center of opening 2104. The distance between two grooves in the second set 2118 of longer grooves is F4.

Figure 22:
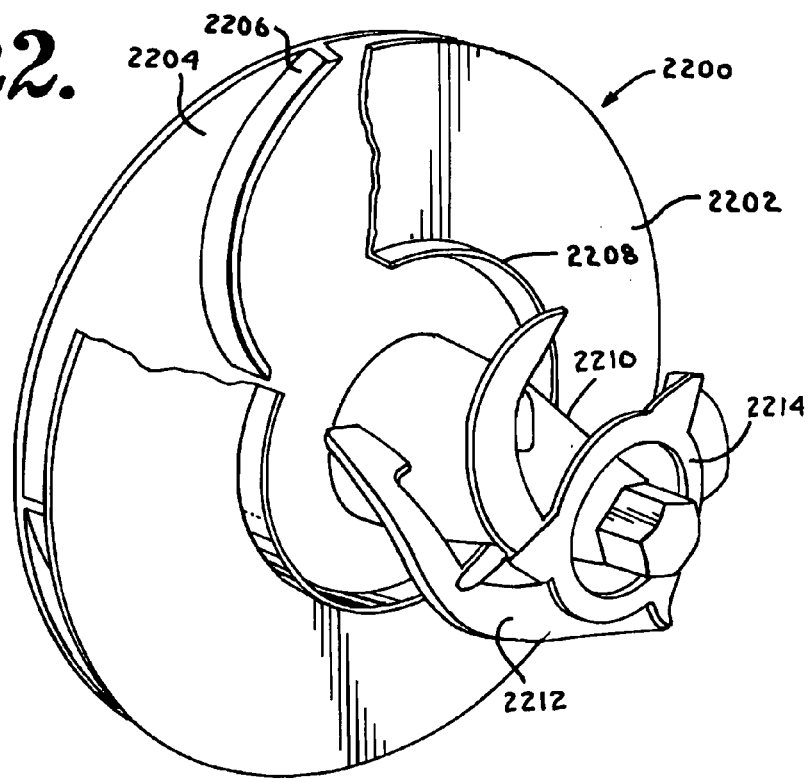
FIG. 22 is a perspective view of a closed rotor with helical blades for increasing suction.

FIG. 22 shows an alternative embodiment of rotor 2200 that is designed to provide increased amounts of suction at the inlet of the apparatus, such as apparatus 10 (FIG. 1), that the rotor is installed within. Rotor 2200 is substantially similar to rotor 1900 shown in FIG. 19. Accordingly, only the differences between the two are discussed herein. Rotor 2200 has a pair of opposed circular plates 2202 and 2204 with vanes 2206 positioned between the plates. Plate 2202 has an opening 2208 for receiving fluid and biomass. Extending through the opening 2208 is a shaft 2210 with three helical shaped blades, one of which is identified as 2212, joined thereto. Each of the blades 2212 extends from a ring 2214 concentric with shaft 2210 to approximately the position where shaft 2210 extends through opening 2208. Blades 2212 increase the suction of material passing through the inlet of the apparatus containing the rotor.

Figure 23:
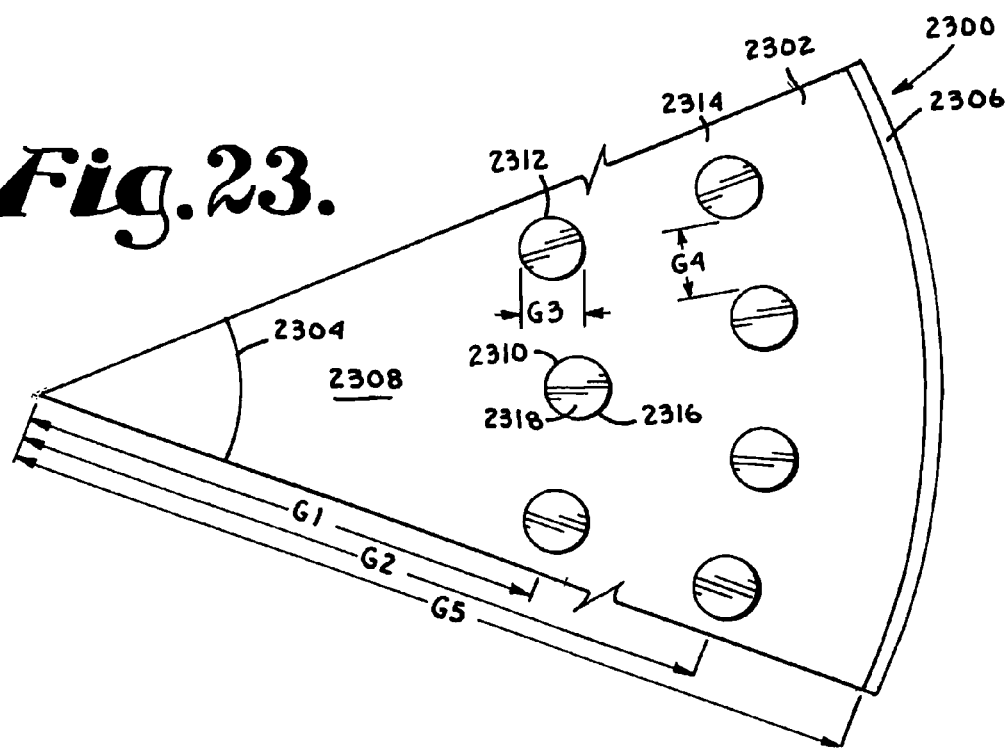
FIG. 23 is a front elevational view of a housing end wall configuration having two rows of cylindrical protrusions.

FIG. 23 shows a portion of a housing end wall configuration that can be used with apparatus 110 (FIG. 4) in place of end wall 114. As shown in FIG. 23, a housing 2300 has an end wall 2302 and an opening 2304 for allowing fluid and biomass to enter the housing. The end wall 2302 of the housing 2300 can be substituted for the end wall 114 shown in FIG. 4. The end wall 2302 extends from opening 2304 to a side wall 2306 of the housing, which is similar to, for example, side wall 28 of the housing shown in FIG. 1. The end wall 2302 comprises a flat surface 2308 between opening 2304 and side wall 2306 and a plurality of protrusions, one of which is identified as 2310, extending outward from surface 2308.

There are first and second rows 2312 and 2314 of protrusions extending outward form surface 2308. Each of the protrusions 2310 is cylindrical with a base that is joined with surface 2308, a side wall 2316 extending outward from surface 2308, and a top surface 2318. The height of each protrusion 2310 is defined as the distance from the base of the protrusion to the top surface 2318. The first row 2312 of protrusions has a radius G1, and the second row 2314 of protrusions has a radius G2. Radiuses G1 and G2 are measured from the center of opening 2304 to the center of the protrusions 2310 in rows 2312 and 2314, respectively. Each of the protrusions has a diameter G3. The distance between adjacent protrusions is G4. The distance G4 may vary between protrusions in the same row and/or between rows 2312 and 2314. The radius from the center of opening 2304 to the side wall 2306 is G5.

When end wall 2302 is positioned opposite a rotor, the first and second rows 2312 and 2314 of protrusions extend toward the rotor. FIG. 4 shows one example of protrusions 112 on an end wall 114 extending toward a rotor 118. Preferably, the first and second rows 2312 and 2314 of protrusions each are positioned between a pair of concentric rows of protrusions on a rotor when in use, in a similar manner as shown in FIG. 4 in which protrusions 112 are positioned in the gaps 120 between the rows of protrusions 122 on rotor 118. By way of further example, if housing 2300 was paired with rotor 1500, preferably, row 2312 would be positioned between rows 1508 and 1510 on rotor 1500, and row 2314 would be positioned between rows 1510 and 1512.

FIG. 24 shows an alternate embodiment of rotor 2400 having a front surface 2402, an opening 2404, which is configured to receive a shaft, and an outer peripheral edge 2406. Opening 2404 has a center 2408. Front surface 2402 comprises a raised flat surface 2409a surrounding opening 2404, an angled surface 2409b adjacent surface 2409a, and a flat surface 2409c positioned below surface 2409a and between surfaces 2409b and edge 2406. There are first, second, third, fourth, and fifth rows 2410, 2412, 2414, 2416, and 2418 of protrusions extending outward from front surface 2402. It is within the scope of the invention for there to be more or less than five rows. For example, in one embodiment the rotor has four rows of protrusions. One of the protrusions in row 2410 is labeled as 2420. Each of the protrusions 2420 in each of rows 2410, 2412, 2414, 2416, and 2418 is a polyhedron. Thus, the protrusions have a polygonal top profile or cross-section.

Each protrusion 2420 has a leading edge 2422 and a trailing edge 2424. The rotor 2400 preferably rotates counter-clockwise in the direction of the leading edge 2422 of the protrusions 2420 such that when the rotor rotates, fluid flows around the protrusions 2420 from the leading edge 2422 to the trailing edge 2424. Each of the protrusions comprises four side walls 2426, 2428, 2430, and 2432 extending upward from front surface 2402, and a top surface 2434 joined with the side walls. As shown in FIG. 24, the relative dimensions of the protrusions' side walls 2426, 2428, 2430, and 2432 preferably varies from row to row. The distance between adjacent protrusions 2420 is shown as H1. This distance between adjacent protrusions can also vary from row to row, or within a single row.

FIG. 25 shows a portion of a housing end wall configuration that can be used with apparatus 110 (FIG. 4) in place of end wall 114. As shown in FIG. 25, a housing 2500 has an end wall 2502 and an opening 2504 for allowing fluid and biomass to enter the housing. The end wall 2502 of the housing 2500 can be substituted for the end wall 114 shown in FIG. 4. The end wall 2502 extends from opening 2504 to a side wall 2506 of the housing, which is similar to, for example, side wall 28 of the housing shown in FIG. 1. The end wall 2502 comprises an angled surface 2507 adjacent opening 2504, a flat surface 2508 between angled surface 2507 and side wall 2506, and a plurality of protrusions, one of which is identified as 2510, extending outward from surface 2508.

There are first, second, third, and fourth rows 2512, 2514, 2516, and 2518 of protrusions extending outward from surface 2508. It is within the scope of the invention for there to be more or less than four rows. For example, in one embodiment, there are three rows of protrusions. Each of the protrusions 2510 is a polyhedron, and most preferably a rectangular prism. Therefore, each protrusion 2510 has four side walls 2520, 2522, 2524, and 2526 extending outward from surface 2508, and a top surface 2528 joined with each of the side walls. The distance between adjacent protrusions 2510 is shown as H2. This distance between adjacent protrusions can vary from row to row, or within a single row.

When end wall 2502 is positioned opposite a rotor, the rows of protrusions 2512, 2514, 2516, and 2518 extend toward the rotor. FIG. 4 shows one example of protrusions 112 on an end wall 114 extending toward a rotor 118. Preferably, the rows of protrusions 2512, 2514, 2516, and 2518 each are positioned between a pair of concentric rows of protrusions on a rotor when in use, in a similar manner as shown in FIG. 4 in which protrusions 112 are positioned in the gaps 120 between the rows of protrusions 122 on rotor 118. By way of further example, if housing 2500 was paired with rotor 2400, preferably, row 2512 would be positioned between rows 2410 and 2412 on rotor 2400, row 2514 would be positioned between rows 2412 and 2414, row 2526 would be positioned between rows 2414 and 2416, and row 2518 would be positioned between rows 2416 and 2418.

FIG. 26 shows an alternative embodiment of rotor 2600 having a front surface 2602, an opening 2604, which is configured to receive a shaft, and an outer peripheral edge 2606. Opening 2604 has a center 2608. Between opening 2604 and edge 2606, there is a raised flat surface 2609a surrounding opening 2604, a cone-like angled surface 2609b adjacent surface 2609a, and a flat surface 2609c between surface 2609b and edge 2606. There are first and second rows 2610 and 2612 of protrusions extending outward from surface 2609b. One of the protrusions is labeled as 2614. Each of the protrusions 2614 is cylindrical with a base that is joined with front surface 2602, a side wall 2616 extending outward from surface 2602, and a top surface 2618. The height of each protrusion 2614 is defined as the distance from the base of the protrusion to the top surface 2618.

A fin 2620 extends outward from one of the protrusions 2614 in the second row 2612. Preferably, there are approximately four fins extending outward from protrusions in the second row 2612; the four fins are preferably equally spaced circumferentially around the rotor. Fin 2620 has a length J1, a width J2, and a height that is approximately the same as the protrusion it extends from. Fin 2620 extends radially outward over the peripheral edge 2606 of the rotor 2600. The structure of fin 2620 improves the rotor's ability to pump incoming fluid out of the apparatus that the rotor 2600 is installed within.

Rotor 2600 has a radius J3 measured from the center 2608 to the outer peripheral edge 2606. The first row 2610 of protrusions has a radius J4, and the second row 2616 of protrusions a radius J5. Radiuses J4 and J5 are measured from the center 2608 to the center of the protrusions 2614 in rows 2610 and 2612, respectively. Each of the protrusions has a diameter J6. The distance between adjacent protrusions is J7. The distance J7 may vary between protrusions in the same row and/or between rows 2610 and 2612.

FIG. 27 shows a portion of a housing end wall configuration that can be used with apparatus 110 (FIG. 4) in place of end wall 114. As shown in FIG. 27, a housing 2700 has an end wall 2702 and an opening 2704 for allowing fluid and biomass to enter the housing. The end wall 2702 of the housing 2700 can be substituted for the end wall 114 shown in FIG. 4. The end wall 2702 extends from opening 2704 to a side wall 2706 of the housing, which is similar to, for example, side wall 28 of the housing shown in FIG. 1. The end wall 2702 comprises an angled surface 2707 adjacent opening 2704, a flat surface 2708 between surface 2707 and side wall 2706, and a plurality of protrusions, one of which is identified as 2710, extending outward from surface 2708.

There is a single row 2712 of protrusions extending outward form surface 2708. Each of the protrusions 2710 is cylindrical with a base that is joined with surface 2708, a side wall 2714 extending outward from surface 2708, and a top surface 2716. The height of each protrusion 2710 is defined as the distance from the base of the protrusion to the top surface 2716. The row 2712 of protrusions has a radius K1, which is measured from the center of opening 2704 to the center of the protrusions 2710. Each of the protrusions has a diameter K2. The distance between adjacent protrusions is K3. The distance K3 may vary between adjacent protrusions in row 2712. The radius from the center of opening 2704 to side wall 2706 is K4.

When end wall 2702 is positioned opposite a rotor, the row 2712 of protrusions extends toward the rotor. FIG. 4 shows one example of protrusions 112 on an end wall 114 extending toward a rotor 118. Preferably, the row 2712 of protrusions is positioned between a pair of concentric rows of protrusions on a rotor when in use, in a similar manner as shown in FIG. 4 in which protrusions 112 are positioned in the gaps 120 between the rows of protrusions 122 on rotor 118. By way of further example, if housing 2700 was paired with rotor 2600, preferably, row 2712 would be positioned between rows 2610 and 2612 on rotor 2600.

Figure 28A:
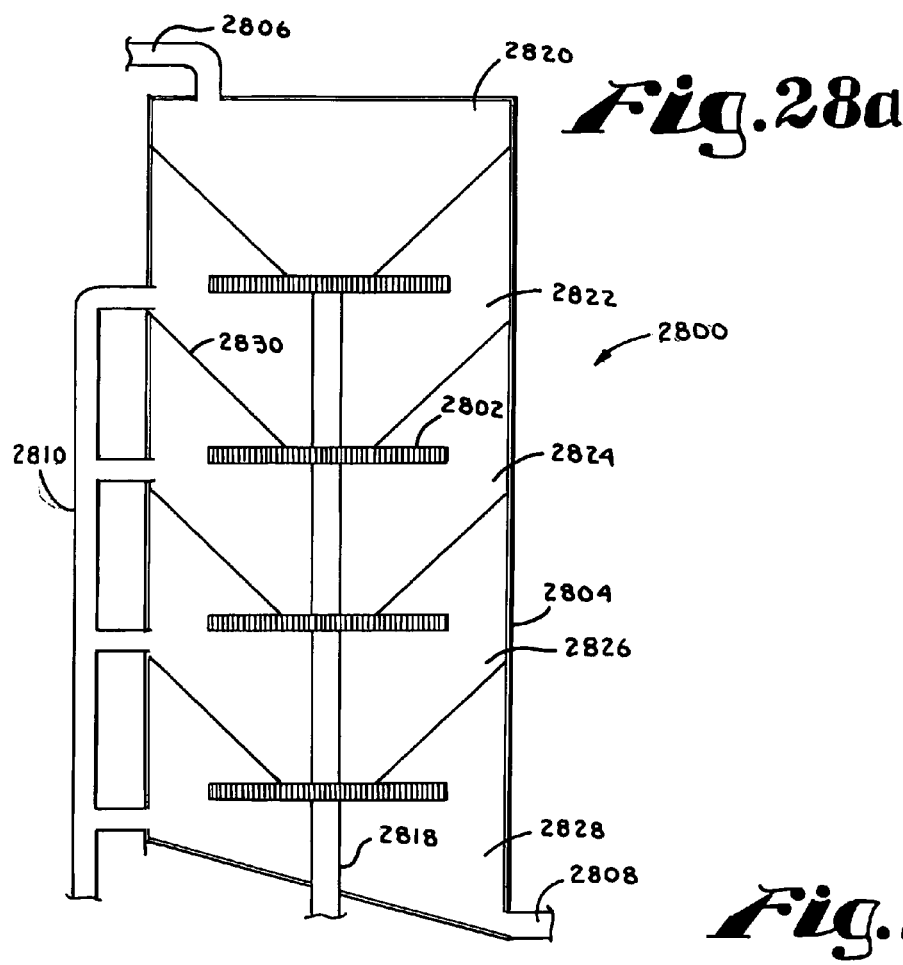
FIG. 28A is a schematic view of a sulfur tower or tank according to the present invention.
Figure 28B:
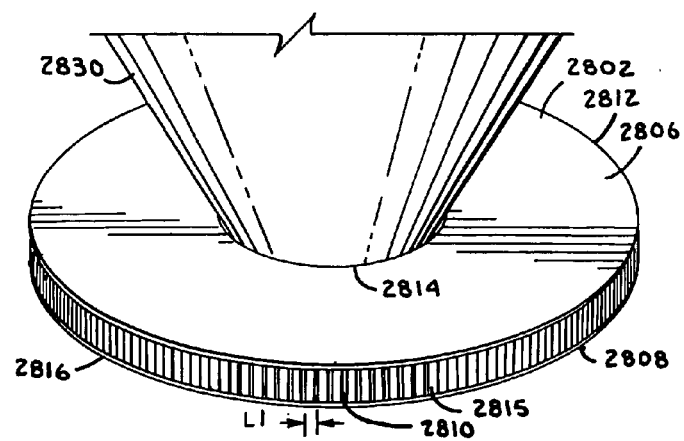
FIG. 28B is a perspective view of a rotor of the sulfur tank shown in FIG. 28A.

FIGS. 28A and 28B show a sulfur tank 2800 and a rotor 2802 according to the present invention. The tank 2800 has a chamber 2804 which contains four of the rotors 2802. The chamber 2804 has an inlet 2806 at the top of the chamber for receiving fluid and biomass and an outlet 2808 at the bottom of the chamber for discharging the fluid and biomass. The bottom of the chamber 2804 is sloped to facilitate the discharge of fluid and biomass through outlet 2808.

A gas/fluid delivery pipe 2810 is in fluid communication with the chamber 2804 for delivering gas or fluid into the interior of the chamber. FIG. 28A shows pipe 2810 having four connections with chamber 2804, although more or less are within the scope of the invention. Pipe 2810 preferably delivers an acidic gas to chamber 2804, and most preferably sulfur dioxide. The delivery of acidic gas to chamber 2804 increases the acidity of fluid contained within the chamber for facilitating the separation of biomass contained within the chamber. Preferably, the biomass separation occurs on a molecular level. Preferably, the tank 2800 is designed for separating molecules of starch and protein within corn endosperm.

Each of the rotors 2802 within chamber 2804 has the same structure as the rotor shown in FIG. 28B. The rotor 2802 has first and second plates 2806 and 2808 that are spaced apart by a plurality of identical cylindrical protrusions, one of which is shown as 2810, that are joined with the plates. First plate 2806 has an outer peripheral edge 2812 and an opening 2814 at its center that is in fluid communication with a void 2815 positioned between the plates. Second plate 2808 has an outer peripheral edge 2816. Referring to FIG. 28A, each of the rotors 2802 is joined to a shaft 2818 for rotation thereby.

Referring to FIG. 28A, chamber 2804 is divided into five sections 2820, 2822, 2824, 2826, and 2828. A rotor 2802 and diverting structure 2830 are positioned between each adjacent section 2820, 2822, 2824, 2826, and 2828. Diverting structure 2830 preferably comprises a funnel that diverts fluid and biomass entering one of the sections 2820, 2822, 2824, and 2826 into the opening 2814 of the rotor 2802 positioned beneath the diverting structure 2830. In this manner, fluid and biomass contained within one section cannot move by gravity to the next lowest section of the chamber 2804 without passing through the opening 2814 of the rotor 2802.

As the rotors 2802 rotate with shaft 2818, fluid and biomass entering the opening 2814 of the rotors 2802 spreads out in a thin sheet along the top surface of the second plate 2808 due to centrifugal force. The force causes the fluid and, biomass to move radially outward along the top surface of the second plate 2808 toward protrusions 2810. Rotors 2802 are preferably rotated with a relatively high rotational velocity such that the fluid and biomass on the top surface of the second plate move rapidly toward protrusions 2810 and impact the protrusions 2810 at a high rate of speed. When the fluid and biomass impact the protrusions 2810, the impact separates or comminutes the biomass and creates a fine mist that emanates from the gaps between the protrusions 2810 as it travels into the next section of the chamber 2804. This process repeats for each of the rotors 2802 within the chamber 2804. Comminuting the biomass in this manner increases the total surface area of the biomass within the tank so that there is more surface area for the acidic gas within the tank to interact with. Increasing the surface area of the biomass speeds up the biomass separation process.

Protrusions 2810 are cylindrical, have a diameter of preferably approximately ⅜ inches and a height of preferably approximately 35 millimeters. Thus, the distance between the first and second plates 2806 and 2808 is preferably approximately 35 millimeters. The spacing or gaps between adjacent protrusions 2810 is shown as L1, and is preferably approximately 4 millimeters. The spacing between adjacent protrusions 2810 is designed to comminute the biomass to a desired size for interaction with the acidic gas within the chamber. The diameters of the first and second plates 2806 and 2808 are preferably approximately 400 millimeters.

FIGS. 29A-D show a method for processing biomass, and most preferably a method for processing corn kernels. The method shown in FIGS. 29A-29D preferably utilizes some or all of the apparatus shown in FIGS. 1-10 and 15-28B and described above. The preferable structure of these apparatus within the method is described in detail after the following description of the flow chart of FIGS. 29A-D. The prefractionation reactors, fractionation reactors, germ and fiber reactor, digestion reactors, and recirculation pumps described below and shown in FIGS. 29A-D preferably comprise one of the apparatus 10, 110, and 210 shown in FIGS. 1-5 having one of the rotors shown in FIGS. 1-9, 15, 17A-20B, 22, 24, and 26 and one of the housing end wall configurations or counter-rotors shown in FIGS. 1-5, 16A-B, 21, 23, 25, and 27. Lines entering these reactors on the flow chart of FIGS. 29A-D indicate material entering the inlet 32 (FIG. 1) of the reactor, and lines exiting the reactors indicate material exiting the outlet 34. The hydrocyclones described below and shown in FIGS. 29A-D preferably comprise a structure similar to the hydrocylone 416 shown in FIG. 10. Lines entering the sides of the hydrocyclones on the flow chart of FIGS. 29A-D indicate material entering the inlet 422 (FIG. 10) of the hydrocyclones, lines exiting the top of the hydrocyclones indicate light material exiting the top outlet 418, and lines exiting the bottom of the hydrocyclones indicate heavy material exiting bottom outlet 420. The sulfur tanks or towers described below and shown in FIGS. 29A-29D preferably comprise a structure similar to the sulfur tank shown in FIGS. 28A-B.

Figure 29A:
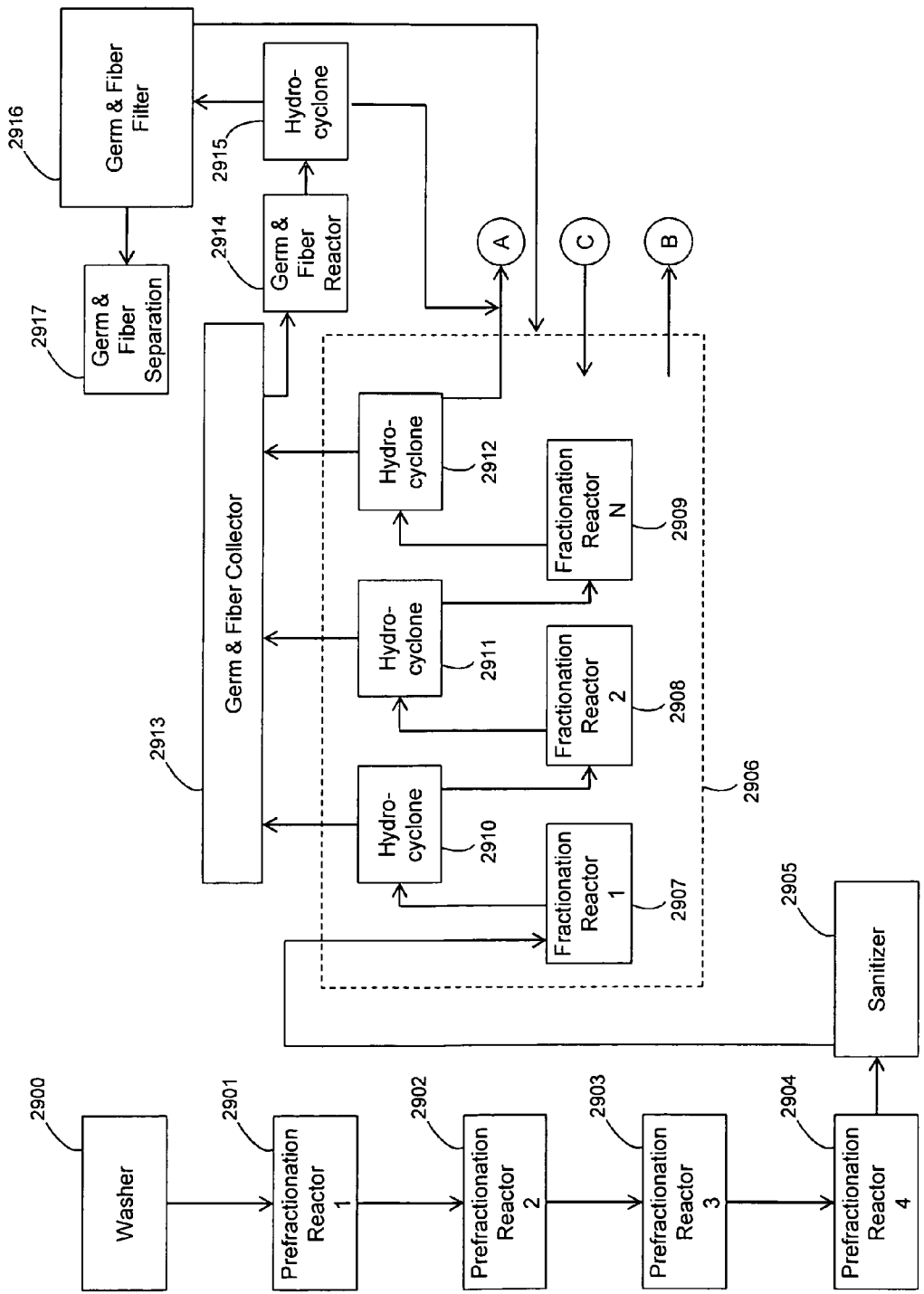
FIGS. 29A-D are a flow chart of a preferred method for processing biomass in accordance with the present invention.

Referring now to FIG. 29A, corn kernels to be processed according to the method of the present invention are first washed in a washer 2900 to remove impurities. Water is then added to the corn before it enters a series of four prefractionation reactors 2901, 2902, 2903, and 2904 that are designed to at least partially separate or blister the pericarp of the kernels from the endosperm. Reactors 2901-2904 are designed to accomplish this separation by generating the forces described above in connection with apparatus 10 from rotation of the rotors within the reactors. Namely, the pericarp is at least partially separated from the endosperm by the combined effects of the rapid creation and implosion of cavitation bubbles formed within the fluid, abrasion between the fluid and corn kernels, abrasion between the corn kernels, impacts between the corn kernels and protrusions within the reactors, and centrifugal force generated by the reactors. The prefractionation reactors 2901-2904 are specially designed to induce cavitation within the fluid medium.

After the series of prefractionation reactors, the water and corn passes to a sanitizer 2905 that washes the corn in two stages. First, the sanitizer 2905 cleans the corn with pressurized water. Then, the sanitizer 2905 cleans the corn with ozonized water. From the sanitizer 2905, the corn passes to a fractionation system 2906, shown generally in dashed lines.

The fractionation system 2906 consists of a fractionation vat that contains water and suspended corn particles, which it receives from other steps in the method as described below. A fluid level sensor monitors the fluid level within the vat. If the fluid level is below a desired level, then water is added to the vat, and if the fluid level is above a desired level, then water exits the vat through path B on FIG. 29A or through a drain in the vat. The fractionation system has a plurality of fractionation reactors 2907, 2908, and 2909 arranged in series, and a plurality of hydrocyclones 2910, 2911, and 2912 that are in fluid communication with the outlets of the fractionation reactors 2907, 2908, and 2909, respectively.

Each of the fractionation reactors 2907, 2908, and 2909 is designed to separate the germ, pericarp, and endosperm of the corn exiting sanitizer 2905. Reactors 2907-2909 accomplish this separation by generating the forces described above in connection with apparatus 10 from rotation of the rotors within the reactors. Namely, the pericarp, germ, and endosperm are separated by the combined effects of the rapid creation and implosion of cavitation bubbles formed within the fluid, abrasion between the fluid and corn kernels, abrasion between the corn kernels, impacts between the corn kernels and protrusions within the reactors, and centrifugal force generated by the reactors.

The inlet of fractionation reactor 2907 is in fluid communication with a pipe that extends up into the fractionation vat and which has an open end within the fractionation vat. Reactor 2907 receives water from the fractionation vat through the open end of this pipe. The outlet of sanitizer 2905 is in fluid communication with a pipe that runs from the sanitizer 2905 into the fractionation vat and which has an open end that is positioned above the open end of the pipe that is joined to the inlet of reactor 2907. The corn and water from sanitizer 2905 travel through the outlet pipe joined with sanitizer 2905 and are discharged through the end of that pipe into the open end of the pipe that is joined to reactor 2907. Thus, reactor 2907 receives corn and water from sanitizer 2905 along with water from within the fractionation vat. The outlet of reactor 2907 is in fluid communication with hydrocyclone 2910, which discharges a light stream of material, preferably pericarp, germ, and water into a germ and fiber collector 2913, and a heavy stream of material, preferably unseparated kernels and endosperm, into the inlet of fractionation reactor 2908 for further separation.

The inlet of fractionation reactor 2908, like reactor 2907, is in fluid communication with a pipe that extends up into the fractionation vat and which has an open end within the fractionation vat for receiving water from the vat. The heavy stream of material exiting hydrocyclone 2910 exits through a pipe that has an open end positioned above the pipe that is joined to the inlet of reactor 2908. Thus, reactor 2908 receives the heavy stream of material from hydrocyclone 2910 along with water from within the fractionation vat. The outlet of reactor 2908 is in fluid communication with a hydrocyclone 2911, which discharges a light stream of material into germ and fiber collector 2913 and a heavy stream of material into fractionation reactor 2909.

Fractionation reactor 2909 represents a plurality of fractionation reactors each having an inlet pipe like reactors 2907 and 2908 and an outlet that is in fluid communication with a hydrocyclone 2912. Preferably, there are five fractionation reactors 2909, such that there are a total of seven fractionation reactors within the fractionation system 2906, and seven hydrocyclones each of which is coupled with the outlet of one of the reactors. The last hydrocyclone 2912 within the system discharges a light stream of material into the germ and fiber collector 2913 and a heavy stream of material (mainly endosperm) that follows the path A on FIG. 29A.

The germ, pericarp (fiber), and water within the germ and fiber collector 2913 is pumped out of the collector with germ and fiber reactor 2914. These components are then passed through a hydrocyclone 2915 which discharges a light stream of germ, pericarp, and water into a germ and fiber filter 2916 and a heavy stream of material, preferably endosperm, that follows the path A. The germ and fiber filter 2916 filters water from the germ and pericarp (fiber) and discharges the filtered germ and pericarp into a germ and fiber separation process 2917 and the water back into the fractionation vat of the fractionation system 2906. The discharged water may contain some endosperm which can be reclaimed within the fractionation system 2906 as it is sucked into reactors 2907-2909 or as it follows path B described below. Germ and fiber separation process 2917 drys the germ and fiber and separates it into separate outlet streams of germ and fiber using conventional processes.

Figure 29B:
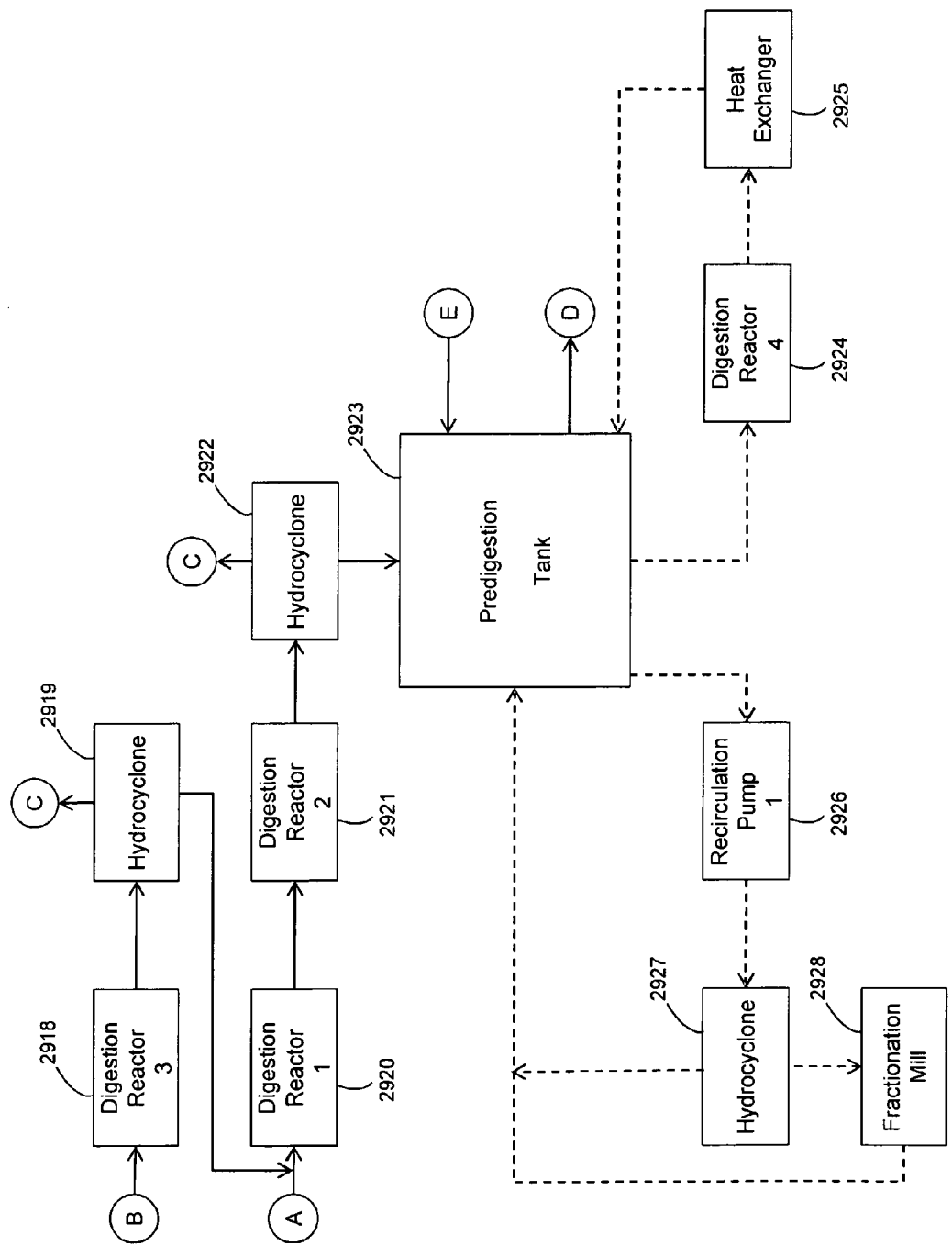

Referring now to FIG. 29B, water and corn particles from the fractionation vat are pumped out of the vat with a digestion reactor 2918. The digestion reactor 2918 discharges the material into a hydrocyclone 2919. The hydrocyclone 2919 discharges a light stream of material back into the fractionation vat through path C and a heavy stream of material into a pair of digestion reactors 2920 and 2921, which also receive the corn endosperm from the hydrocyclones 2912 and 2915 in the fractionation system 2906.

Starting with digestion reactor 2920 the endosperm and water slurry exiting hydrocyclones 2912, 2915, and 2919 begins a digestion process that is designed to separate the starch, protein, and fiber contained within the endosperm on a molecular level. The digestion process includes a number of digestion reactors that are designed to reduce the size of the suspended endosperm solids within the endosperm/water slurry so that acidic gas introduced to the slurry within sulfur tanks acts on a greater surface area of the endosperm molecules. The digestion reactors also generate the forces described above in connection with apparatus 10 from rotation of the rotors within the reactors. The endosperm slurry also passes through heat exchangers that are designed to heat the slurry to a temperature just below the temperature at which the starch within the slurry gelatinizes. The heat exchangers are preferably positioned and designed to maintain the slurry at a temperature of between approximately 30 to 52 degrees Celsius and most preferably at a temperature of approximately 51 degrees Celsius. Increasing the heat of the slurry, in combination with the acidic environment of the sulfur tanks and the reduction of suspended solid particle size, facilitates the separation of starch and protein molecules within the slurry without degrading the starch into undesirable sugars. The digestion process is described in detail below.

Digestion reactors 2920 and 2921 are designed to comminute the corn endosperm within the endosperm slurry exiting hydrocyclones 2912, 2915, and 2919. The endosperm slurry exiting digestion reactor 2921 enters a hydrocyclone 2922, which discharges a light stream of material, preferably any germ and pericarp remaining in the endosperm slurry, back to the fractionation vat along a path C, and a heavy stream of material, preferably endosperm to a predigestion holding tank 2923.

The predigestion tank 2923 has two optional feedback loops that may be activated depending on the characteristics of the endosperm slurry contained within the tank. First, a valve may be opened to allow the slurry to pass into a digestion reactor 2924, which further comminutes the slurry, and a heat exchanger 2925, which heats the slurry, before it returns to tank 2923. In another loop, the slurry enters a recirculation pump 2926, which sends the slurry to a hydrocyclone 2927. Hydrocyclone 2927 passes light material back to the predigestion tank 2923 and heavy material into a fractionation mill 2928 that further grinds the endosperm slurry before discharging it back to tank 2923.

Figure 29C:
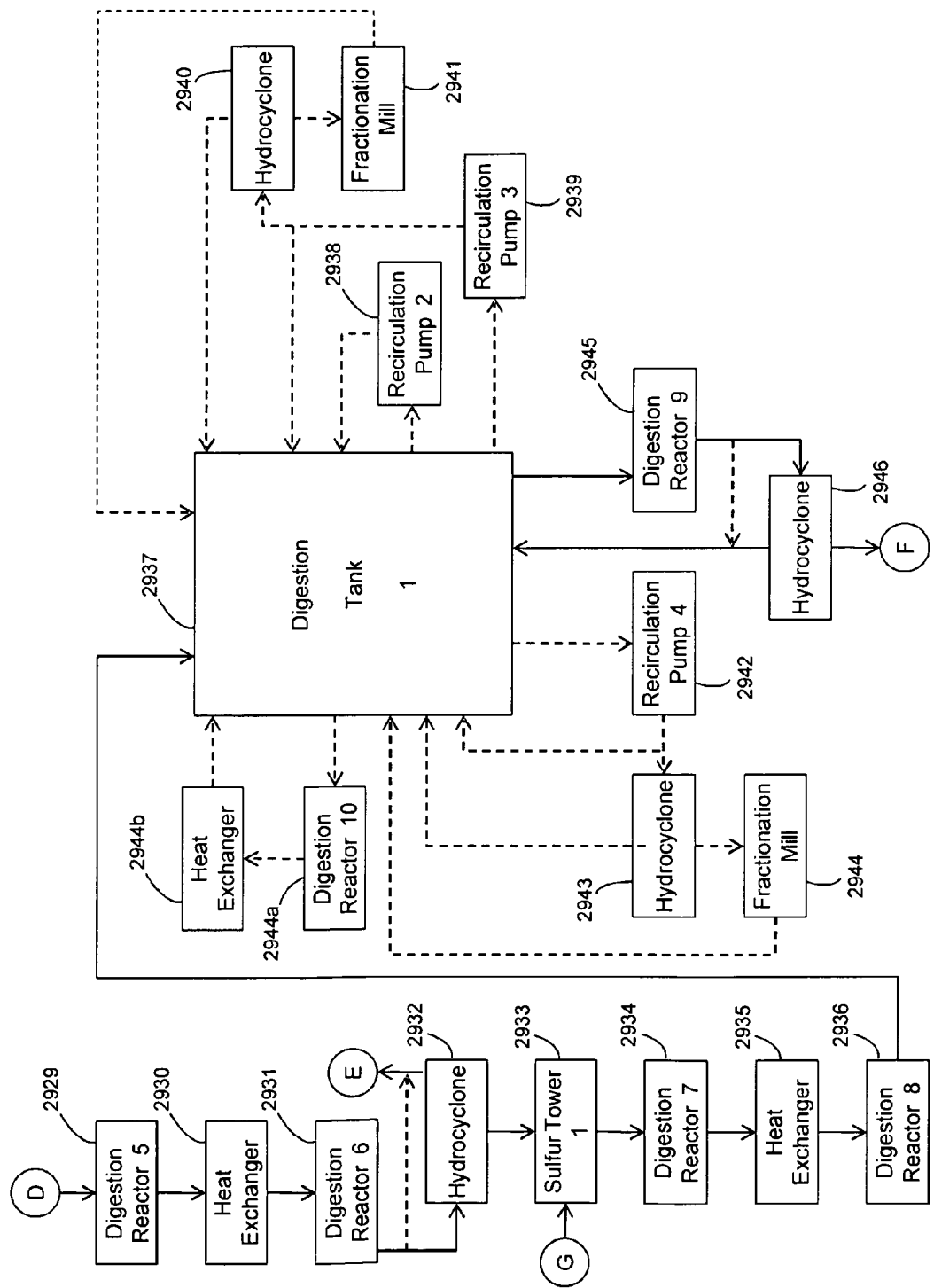
Figure 29D:
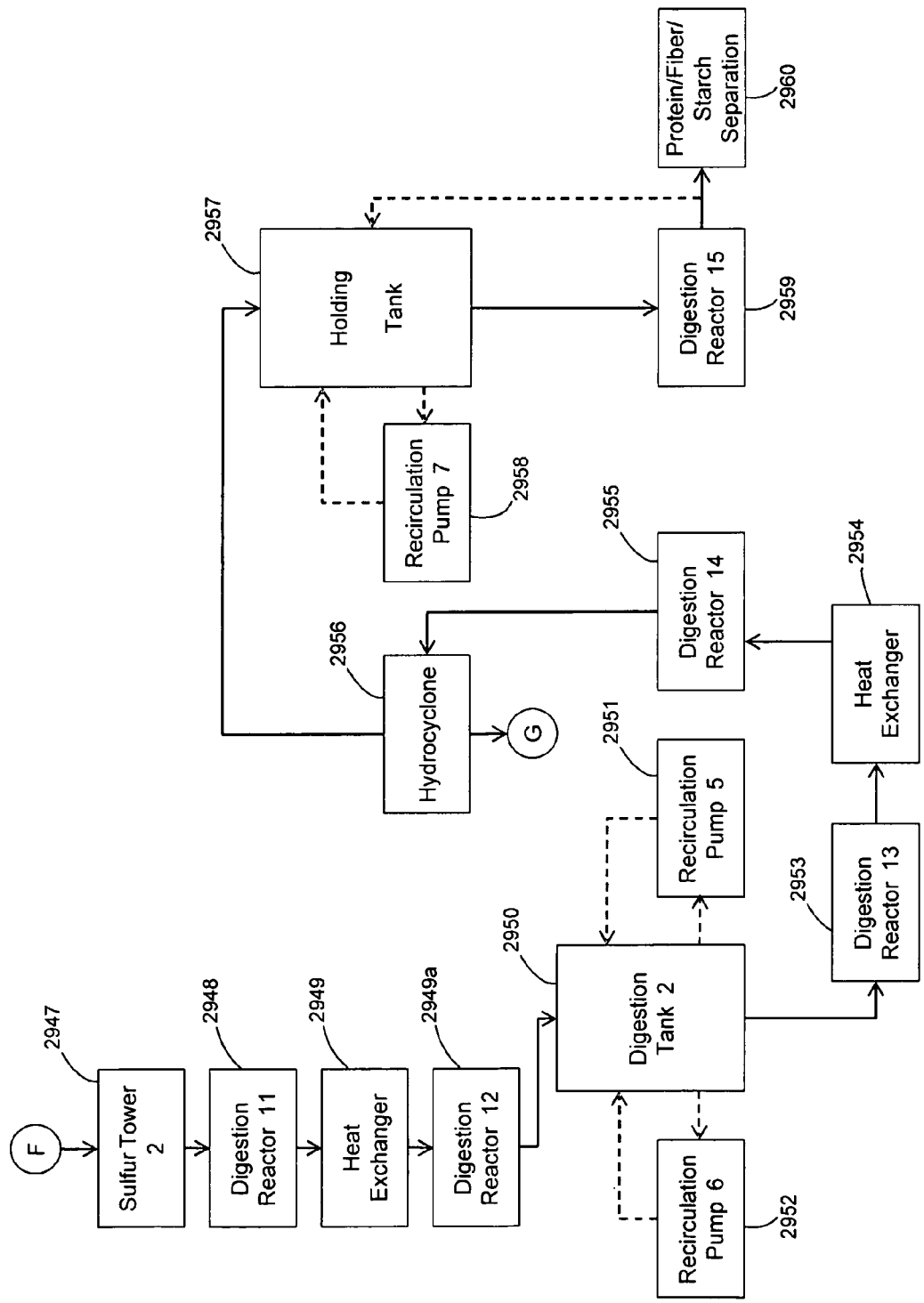

Tank 2923 discharges the endosperm slurry through path D on FIG. 29B to a digestion reactor 2929 on FIG. 29C, which further comminutes the slurry. The slurry travels from reactor 2929 to a heat exchanger 2930, which preferably heats the slurry to a temperature that is just below the temperature at which starch in the slurry gelatinizes, which is preferably between approximately 30 to 52 degrees Celsius, and most preferably approximately 51 degrees Celsius. From heat exchanger 2930, the slurry travels to another digestion reactor 2931, which further comminutes the slurry and discharges it into a hydrocyclone 2932. Hydrocyclone 2932 discharges a light stream of material into predigestion tank 2923 along path E and a heavy stream of material into sulfur tower 2933. Optionally, via a valve positioned between reactor 2931 and hydrocyclone 2932, slurry exiting reactor 2931 is directed along path E to tank 2923.

Sulfur tower 2933 preferably has a structure as described above in connection with sulfur tank 2800 shown in FIG. 28. The sulfur tower 2933 is designed to increase and/or maintain the acidity and temperature of the endosperm and water slurry contained within the tower. The sulfur tower 2933 is also designed to comminute the endosperm slurry into a fine mist in order to increase the surface area of the slurry. The acidic environment, temperature, and comminution of endosperm slurry within the sulfur tower 2933 facilitates the separation of the starch and protein molecules contained within the endosperm slurry. Preferably, the sulfur tower 2933 maintains the acidity of the endosperm slurry at a pH of between approximately 2 to 6, more preferably at a pH of between approximately 3.8 to 4.5, and most preferably at a pH of approximately 3.8. The target pH level is designed to facilitate separation of the starch and protein molecules without reducing the quality of the end product produced by the method. The sulfur tower 2933 preferably receives sulfur dioxide gas in order to maintain the acidity of the endosperm slurry at a desired level. The slurry within tower 2933 is preferably approximately 80% water and 20% suspended solids.

The slurry exits sulfur tower 2933 and enters a digestion reactor 2934, a heat exchanger 2935, and a digestion reactor 2936, which are designed to further comminute the slurry and maintain its temperature at the desired range. The slurry then travels from digestion reactor 2936 to digestion tank 2937. In digestion tank 2937, the starch and protein molecules within the acidified and heated slurry continue to separate. The digestion tank 2937 maintains the heat of the slurry at the desired range specified above. Preferably, tank 2937 has a hot water jacket for maintaining the slurry's temperature.

The digestion tank 2937 also contains four optional feedback loops that may be activated depending on the characteristics of the slurry contained within the tank. First, the slurry may be pumped from one level of the tank to another via a recirculation pump 2938. Second, slurry within the tank may be pumped through a recirculation pump 2939 into a hydrocyclone 2940. Optionally, via a valve positioned between pump 2939 and hydrocyclone 2940, the slurry may be pumped back into tank 2937 with pump 2939. Hydrocyclone 2940 discharges light material back into digestion tank 2937 and heavy material into a fractionation mill 2941, which further comminutes the slurry before sending it back to the digestion tank 2937. Third, slurry within tank 2937 is pumped through a recirculation pump 2942 into a hydrocyclone 2943. Optionally, via a valve positioned between pump 2942 and hydrocyclone 2943, the slurry may be pumped back into tank 2937 with pump 2942. Hydrocyclone 2943 discharges light material back into digestion tank 2937 and heavy material into a fractionation mill 2944, which further comminutes the slurry before sending it back to tank 2937. Lastly, slurry is pumped from one level of the tank 2937 through digestion reactor 2944*a* and heat exchanger 2944*b* and back to another level of the tank.

Endosperm slurry exits digestion tank into a digestion reactor 2945, which further comminutes the slurry and sends it to a hydrocyclone 2946. Optionally, via a valve positioned between reactor 2945 and hydrocyclone 2946, the slurry may be pumped back into tank 2937 with reactor 2945. Hydrocyclone 2946 discharges a light stream of material back into tank 2937 and a heavy stream of material through path F to a second sulfur tower 2947 shown on FIG. 29D.

Sulfur tower 2947 preferably has a similar structure and functions in the same manner as sulfur tower 2933 on FIG. 29C. Accordingly, sulfur tower 2947 will not be described in detail herein. The slurry travels from sulfur tower 2947 through a digestion reactor 2948 into a heat exchanger 2949. From heat exchanger 2949, the slurry passes through a digestion reactor 2949*a* on its way to a second digestion tank 2950, which maintains the temperature of the slurry in a similar manner as digestion tank 2937. Digestion tank 2950 has two optional feedback loops. Two recirculation pumps 2951 and 2952 may pump slurry from one level of the tank to another level.

The slurry then exits digestion tank 2950 and travels through a digestion reactor 2953 into a heat exchanger 2954. From heat exchanger 2954, the slurry is pumped by a digestion reactor 2955 into a hydrocyclone 2956. Hydrocyclone 2956 discharges lighter digested slurry into the top of a holding tank 2957 and heavier undigested slurry back to the first sulfur tower 2933 (FIG. 29C) along path G for further digestion. Holding tank 2957 maintains the temperature of the slurry within the desired range specified above in a similar manner as tanks 2937 and 2950. Tank 2957 also has an optional feedback loop consisting of a recirculation pump 2958 that pumps the slurry between levels of the tank 2957.

The slurry exits tank 2957 through a digestion reactor 2959 that pumps the slurry into a protein/fiber/starch separation process 2960. Optionally, via a valve positioned between reactor 2959 and process 2960, the slurry is returned to holding tank 2957 from reactor 2959. The protein/fiber/starch separation process 2960 divides the separated endosperm protein, starch, and fiber within the endosperm slurry into separate streams of protein, starch, and fiber using conventional processes and equipment.

With the process of the present invention it takes between approximately 5 minutes to 2 hours to separate the pericarp, germ, and endosperm of corn kernels into an endosperm stream and a pericarp and germ stream, as well as to separate starch and protein molecules in the endosperm stream. The prefractionation process of passing the corn kernels through prefractionation reactors 2901, 2902, 2903, and 2904 takes between approximately 2 to 4 seconds, and most preferably approximately 3 seconds. The fractionation process of fractionation system 2906 takes between approximately 6 to 17 seconds, and most preferably approximately 7 seconds to separate the germ, pericarp, and endosperm of the corn kernels into an endosperm stream that enters the digestion process at reactor 2920 and a pericarp and germ stream that enters the germ and fiber separation process 2917. The digestion process from digestion reactor 2920 to the protein/fiber/starch separation process 2960 takes between approximately 5 minutes to 3 hours depending on the type of corn being processed, and most preferably between 5 minutes to 2 hours. The harder the endosperm, the longer the digestion process takes. After centrifugation or decantation of the endosperm stream during the protein/fiber/starch separation process 2960, the process can yield a relatively pure starch stream that contains only approximately 0.35% protein or less.

The preferable structure and dimensions of the reactors shown in FIGS. 29A-29D is as follows. Each of the rotors in the reactors preferably rotates in a counter-clockwise direction. The dimensions given below are only preferable dimensions and may vary by any amount. For example, the dimensions may vary by between 0-50%. Further, the dimensions may vary by 25%, 15%, 10%, or 5%.

Prefractionation reactor 2901 preferably has a rotor 1500, as shown in FIG. 15, and a housing end wall configuration 1600, as shown in FIG. 16. The rotor 1500 in reactor 2901 preferably has the following dimensions: A5—⅜ inches, and A6—11 mm. The height of the protrusions 1514 is preferably approximately 10 mm. The dimensions B1-B4 for end wall 1600 are preferably approximately as follows: B1—1.5 mm, B2—from 3 mm adjacent section 1612 to 2 mm adjacent section 1608, B3—79 mm, and B4—161 mm.

Prefractionation reactor 2902 preferably has a rotor 1500, as shown in FIG. 15, and a housing end wall configuration with a flat surface. The dimensions A5-A6 for the rotor 1500 in reactor 2902 are preferably approximately as follows: A5—⅜ inches, and A6—9.5 mm. The height of the protrusions 1514 is preferably approximately 10 mm.

Prefractionation reactor 2903 preferably has a rotor 1500, as shown in FIG. 15, and a housing end wall configuration 1600, as shown in FIG. 16. The dimensions A5-A6 for the rotor 1500 in reactor 2903 are preferably approximately as follows: A5—⅜ inches, and A6—11 mm. The height of the protrusions 1514 is preferably approximately 10 mm. The dimensions B1-B4 for end wall 1600 are preferably approximately as follows: B1—1.5 mm, B2—2 mm, B3—70 mm, and B4—160 mm.

Prefractionation reactor 2904 preferably has a rotor 1700, as shown in FIG. 17A, and a housing end wall configuration with a flat surface. The dimensions C5-C6 for the rotor 1700 in reactor 2904 are preferably approximately as follows: C5—½ inches, and C6—12 mm. The height of the protrusions 1514 is preferably approximately 7.5 mm.

Fractionation reactor 2907 preferably has a rotor 1800, as shown in FIGS. 18A-B, and a housing end wall configuration with a flat surface. The dimensions for the first row 1810 of protrusions for the rotor 1800 in reactor 2907 are preferably approximately as follows: D1—13.5 mm, D3—8 mm, and D8—½ inches. The dimensions for the second row 1812 of protrusions are preferably approximately as follows: D2—6.5 mm, D3—17 mm, and D8—½ inches. The dimensions for the third row 1814 of protrusions are preferably approximately as follows: D2—7 mm, D3—19 mm, and D8—½ inches.

Fractionation reactor 2908 preferably has a rotor 1800, as shown in FIGS. 18A-B, and a housing end wall configuration with a flat surface. The dimensions for the first row 1810 of protrusions for the rotor 1800 in reactor 2908 are preferably approximately as follows: D1—17 mm, D3—9 mm, and D8—⅜ inches. The dimensions for the second row 1812 of protrusions are preferably approximately as follows: D2—9 mm, D3—17 mm, and D8—½ inches. The dimensions for the third row 1814 of protrusions are preferably approximately as follows: D2—9 mm, D3—17.5 mm, and D8—½ inches.

Fractionation reactor 2909 preferably comprises a series of five reactors, as set forth above. The first of those reactors preferably has a rotor 1750, as shown in FIG. 17B, and a housing end wall configuration with a flat surface. The dimensions for the first row 1752 of protrusions are preferably approximately as follows, making reference to similar dimensions on FIG. 17A: C5—½ inches, C6—14 mm, and a protrusion height of 8 mm. The dimensions for the second row 1754 of protrusions are preferably approximately as follows: C5—½ inches, C6—12.5 mm, and a protrusion height of 8 mm. The dimensions for the third row 1756 of protrusions are preferably approximately as follows: C5—½ inches, C6—12 mm, and a protrusion height of 8 mm. The dimensions C1-C4 for each of the five reactors 2909 are preferably approximately as follows: C1—177 mm, C2—90 mm, C3—130 mm, and C4—170 mm.

The second of reactors 2909 preferably has a rotor 1700, as shown in FIG. 17A, and a housing end wall configuration with a flat surface. The dimensions for the first row 1710 of protrusions are preferably approximately as follows: C5—½ inches, C6—9.5 mm, and a protrusion height of 8 mm. The dimensions for the second row 1712 of protrusions are preferably approximately as follows: C5—½ inches, C6—9 min, and a protrusion height of 8.5 mm. The dimensions for the third row 1714 of protrusions are preferably approximately as follows: C5—½ inches, C6—8 mm, and a protrusion height of 9.5 mm.

The third of reactors 2909 preferably has a rotor 1700, as shown in FIG. 17A, and a housing end wall configuration with a flat surface. The dimensions for the first row 1710 of protrusions are preferably approximately as follows: C5—½ inches, C6—9.5 mm, and a protrusion height of 8 mm. The dimensions for the second row 1712 of protrusions are preferably approximately as follows: C5—½ inches, C6—9 mm, and a protrusion height of 8 mm. The dimensions for the third row 1714 of protrusions are preferably approximately as follows: C5—½ inches, C6—7.5 mm, and a protrusion height of 8 mm.

The fourth of reactors 2909 preferably has a rotor 1700, as shown in FIG. 17A, and a housing end wall configuration with a flat surface. The dimensions for the first row 1710 of protrusions are preferably approximately as follows: C5—½ inches, C6—7.5 mm, and a protrusion height of 8.5 mm. The dimensions for the second row 1712 of protrusions are preferably approximately as follows: C5—½ inches, C6—7 mm, and a protrusion height of 8.5 mm. The dimensions for the third row 1714 of protrusions are preferably approximately as follows: C5—½ inches, C6—7.5 mm, and a protrusion height of 8.5 mm.

The fifth of reactors 2909 preferably has a rotor 1700, as shown in FIG. 17A, and a housing end wall configuration with a flat surface. The dimensions for the first, second, and third rows 1710 of protrusions are preferably approximately as follows: C5—½ inches, C6—6.5 mm, and a protrusion height of 8 mm.

Germ and fiber reactor 2914 preferably has a rotor 1900, as shown in FIG. 19, and a housing end wall configuration with a flat surface. The rotor 1900 preferably has an external diameter of approximately 300 mm.

Digestion reactor 2920 preferably has a rotor 2000, as shown in FIGS. 20A-B, and a housing end wall configuration 2100, as shown in FIG. 21. The dimensions for rotor 2000 are preferably approximately as follows: E2—151 mm, E4—20 mm, E5—10 to 11 mm, E6—3 mm, E7—3 mm, and E8—3 mm. The distance between vanes 2020 is preferably approximately 11 mm. The vanes 2028 preferably have a height of approximately 8 mm. The width of the grooves 2014 and 2016 is preferably approximately 6 mm and 5.5 mm, respectively. The length of the grooves 2014 is preferably approximately 64 mm. The dimensions for end wall 2100 are preferably approximately as follows: F1—78 mm, F2—155 mm, and F4—31.5 mm. The width of each of grooves 2116 and 2118 is preferably approximately 9 mm. The length of grooves 2116 and 2118 is preferably approximately 75.5 and 99 mm, respectively.

Digestion reactor 2921 preferably has a rotor 2000, as shown in FIGS. 20A-B, with the exception that there are no vanes 2020 and 8 vanes 2028, and a housing end wall configuration 2100, as shown in FIG. 21. The dimensions for rotor 2000 are preferably approximately as follows: E2—147 mm, E4—30 mm, E5—10 mm, and E6—3 mm. The vanes 2028 preferably have a height of approximately 7.5 mm. The width of each of grooves 2014 and 2016 is preferably approximately 8 mm. The length of the grooves 2014 is preferably approximately 65 mm. The dimensions for end wall 2100 are preferably approximately as follows: F1—70 mm, F2—155 mm, and F4—35 mm. The width of each of grooves 2116 and 2118 is preferably approximately 7.5 mm. The length of grooves 2116 and 2118 is preferably approximately 82 and 96 mm, respectively.

Digestion reactor 2918 preferably has a rotor 2200, as shown in FIG. 22. The rotor 2200 preferably has an external diameter of approximately 295 mm.

Digestion reactor 2924 preferably has a rotor 2000, as shown in FIGS. 20A-B, with the exception that there are no vanes 2020, and a housing end wall configuration 2100, as shown in FIG. 21. The dimensions for rotor 2000 in reactor 2924 are preferably approximately as follows: E2—147 mm, E4—32 mm, E5—9 mm, and E6—3 mm. The vanes 2028 preferably have a height of approximately 7.5 mm. The width of grooves 2014 is preferably approximately 6 mm, and the width of grooves 2016 is preferably approximately 5.5 mm. The length of grooves 2014 is preferably approximately 54 mm, and the length of grooves 2016 is preferably approximately 124 mm. The dimensions for end wall 2100 are preferably approximately: F2—159 mm. The width of grooves 2116 is preferably approximately 4.5 mm, and the width of grooves 2118 is preferably approximately 5.3 mm.

Digestion reactors 2929, 2931, 2945, and 2944a each preferably have a rotor 1500, as shown in FIG. 15, and a housing end wall configuration 2300, as shown in FIG. 23. The rows 2312 and 2314 on end wall 2300 are positioned between rows 1508 and 1510 and rows 1510 and 1512, respectively.

For digestion reactor 2929, rotor 1500 preferably has approximately the following dimensions: A1—200 mm, A2—113 mm, A3—152 mm, A4—190 mm, A5—17 mm, A6—15 mm for row 1508, 14 mm for row 1510, and 16 mm for row 1512, and A7—12 mm. The height of the protrusions is preferably approximately 8 mm. The dimensions for end wall 2300 are preferably approximately: G1—132 mm, G2—170 mm, G3—13 mm, G4—13 mm, and G5—201 mm. The height of the protrusions 2310 is preferably approximately 7 mm.

For digestion reactor 2931, rotor 1500 preferably has approximately the following dimensions: A1—199 mm, A2—114 mm, A3—152 mm, A4—190 mm, A5—17 mm, A6—15 mm for rows 1508 and 1510 and 16 mm for row 1512, and A7—12 mm. The height of the protrusions is preferably approximately 7 mm. The dimensions for end wall 2300 are preferably approximately: G1—133 mm, G2—171 mm, G3—13 mm, G4—13 mm, and G5—192 mm. The height of the protrusions 2310 is preferably approximately 9 mm.

For digestion reactors 2945 and 2944a, the dimensions for the rotor 1500 are preferably approximately as follows: A5—17 mm, A6—15 mm for rows 1508 and 1510 and 16 mm for row 1512, and A7—12 mm. The height of the protrusions 1514 is preferably approximately 7.5 mm. The dimensions for end wall 2300 are preferably approximately: G3—½ inches, and G4—8 mm for row 2312 and 7 mm for row 2314. The height of the protrusions 2310 is preferably approximately 7.5 mm.

Digestion reactor 2934 preferably has a rotor 2400, as shown in FIG. 24, and a housing end wall configuration 2500, as shown in FIG. 25. The rows 2512, 2514, 2516, and 2518 on end wall 2500 are positioned between the rows on 2410, 2412, 2414, 2416, and 2418 on rotor 2400 as described above. The distance H1 between adjacent protrusions 2420 on rotor 2400 is preferably approximately 6.5 or 8 mm. The distance H2 between adjacent protrusions 2510 on end wall 2500 is preferably approximately 6.5 or 8 mm.

Digestion reactor 2936 preferably has a rotor 2400, as shown in FIG. 24, and a housing end wall configuration 2500, as shown in FIG. 25, with the exceptions that the rotor 2400 only has four rows of protrusions and the end wall 2500 only has three rows of protrusions. The rows on the end wall 2500 are positioned between the rows on the rotor 2400 as described above. The distance H1 between adjacent protrusions 2420 on rotor 2400 is preferably approximately 13 mm. The distance H2 between adjacent protrusions 2510 on end wall 2500 is preferably approximately 13 mm.

Digestion reactor 2948 preferably has a rotor 1500, as shown in FIG. 15, and a housing end wall configuration 2300, as shown in FIG. 23. Row 2312 on end wall 2300 is positioned between rows 1508 and 1510 on rotor 1500, and row 2314 is positioned between rows 1510 and 1512. The dimensions A1-A6 for the rotor 1500 are preferably approximately: A1—200 mm, A2—114 mm, A3—152 mm, A4—190 mm, A5—17 mm, and A6—16.5 mm. The height of the protrusions 1514 is preferably approximately 8.8 mm. The dimensions G1-G5 for end wall 2300 are preferably approximately: G1—133 mm, G2—175 mm, G3—12.7 mm, G4—13 mm, and G5—201 mm. The height of the protrusions 2310 is preferably approximately 7.6 mm.

Digestion reactor 2949a preferably has a rotor 1700 as shown in FIG. 17A, and a housing end wall configuration 2300, as shown in FIG. 23. Row 2312 on end wall 2300 is positioned between rows 1710 and 1712 on rotor 1500, and row 2314 is positioned between rows 1712 and 1714. The dimensions C1-C6 for rotor 1700 are preferably approximately: C1—190 mm, C2—140 mm, C3—163 mm, C4—185 mm, C5—11.2 mm, and C6—8.5 mm for row 1714 and 7.8 mm for rows 1710 and 1712. The height of the protrusions 1716 is preferably approximately 7.8 mm. Six of the protrusions 1716 on row 1714 also preferably have a fin 2620 (FIG. 26) with a length J1 of 9.5 mm, a thickness J2 of 4 mm, and a height of 16.2 mm. The dimensions G1-G5 for end wall 2300 are preferably approximately: G1—152 mm, G2—174 mm, G3—7.8 mm, G4—11.8 mm for row 2314 and 11.6 mm for row 2312, and G5—201 mm. The height of the protrusions 2310 is preferably approximately 7.3 mm.

Digestion reactor 2953 preferably has a rotor 1700 as shown in FIG. 17A, and a housing end wall configuration 2300, as shown in FIG. 23. Row 2312 on end wall 2300 is positioned between rows 1710 and 1712 on rotor 1500, and row 2314 is positioned between rows 1712 and 1714. The dimensions C1-C6 for rotor 1700 are preferably approximately: C1—191 mm, C2—141 mm, C3—163 mm, C4—185 mm, C5—10 mm, and C6—9.7 mm for row 1714 and 9.0 mm for rows 1710 and 1712. The height of the protrusions 1716 is preferably approximately 7.4 mm. Six of the protrusions 1716 on row 1714 also preferably have a fin 2620 (FIG. 26) with a length J1 of 9 mm, a thickness J2 of 4 mm, and a height of 13 mm. The dimensions G1-G5 for end wall 2300 are preferably approximately: G1—152 mm, G2—174 mm, G3—9.5 mm, G4—10.2 mm, and G5—201 mm. The height of the protrusions 2310 is preferably approximately 7.5 mm.

Digestion reactor 2955 preferably has a rotor 1700 as shown in FIG. 17A, and a housing end wall configuration 2300, as shown in FIG. 23. Row 2312 on end wall 2300 is positioned between rows 1710 and 1712 on rotor 1500, and row 2314 is positioned between rows 1712 and 1714. The dimensions C1-C6 for rotor 1700 are preferably approximately: C1—191 mm, C2—141 mm, C3—163 mm, C4—185 mm, C5—9.5 mm, and C6—10.2 mm for row 1714 and 9.5 mm for rows 1710 and 1712. The height of the protrusions 1716 is preferably approximately 7.2 mm. Six of the protrusions 1716 on row 1714 also preferably have a fin 2620 (FIG. 26) with a length J1 of 9 mm, a thickness J2 of 4 mm, and a height of 15 mm. The dimensions G1-G5 for end wall 2300 are preferably approximately: G1—152 mm, G2—174 mm, G3—9.6 mm, G4—10.1 mm for row 2314 and 9.4 mm for row 2312, and G5—201 mm. The height of the protrusions 2310 is preferably approximately 7.2 mm.

Digestion reactor 2959 preferably has a rotor 1500, as shown in FIG. 15, and a housing end wall configuration 2300, as shown in FIG. 23. Preferably, the rotor 1500 has approximately the following dimensions: A1—178 mm, A2—91 mm, A3—129 mm, A4—169 mm, A5—⅜ inches, and A6—8 mm. The height of the protrusions 1514 is preferably approximately 11 mm. Preferably, the end wall 2300 has approximately the following dimensions: G1—110 mm, G2—149 mm, G3—⅜ inches, G4—11 mm, and G5—190 mm. The height of the protrusions 2310 is preferably approximately 11 mm.

Recirculation pumps 2926, 2938, 2939, 2942, 2951, 2952, and 2958 preferably have a rotor 2600, as shown in FIG. 26, and a housing end wall configuration 2700, as shown in FIG. 27. Preferably, the rotor 2600 has approximately the following dimensions: J1—10.3 mm, J2—2.2 mm, J3—88 mm, J4—56 mm, J5—79 mm, J6—9.7 mm, J7—11.3 mm. The protrusions 2610 preferably have a height of approximately 19.6 mm. The vanes 2620 preferably have a height of approximately 27 mm. Preferably, the end wall 2700 has the following dimensions: K1—68 mm, K2—9.6 mm, K3—14.2 mm, and K4—94 mm. The protrusions 2710 preferably have a height of approximately 20.6 mm.

Preferably, the feed rate for the process shown in FIGS. 29A-D starting at washer 2900 is approximately 14.5 metric tons of corn per hour at 12% moisture, which is approximately equivalent to 12.76 metric tons on a dry matter basis. The preferable minimum feed rate for the process is approximately 8 metric tons per hour at 12% moisture. The percentage of the corn that is transferred to sulfur tower 2933 is between approximately 75 to 84%, the majority of the remainder passing to germ and fiber separation process 2917. Heat exchangers 2930, 2935, 2944b, 2949, and 2954 and the hot water jackets of digestion tanks 2937 and 2950 preferably receive hot water at approximately 52 degrees Celsius for maintaining and/or increasing the temperature of the slurry at the levels described above, which are preferably between 30 to 52 degrees Celsius.

The ratio of water to solid material in the endosperm slurry throughout the digestion stage of the process beginning at sulfur tower 2933 to digestion tank 2950 is approximately between 5:1 to 7:1 and most preferably approximately 6:1. The water to solid ratio of the slurry entering the protein/fiber/starch separation process 2960 is preferably approximately between 8:1 to 12:1 and most preferably is approximately 10:1. Sulfur towers 2933 and 2947 preferably process approximately 11.6 metric tons of endosperm per hour. The heat exchangers preferably have a capacity of approximately 105 cubic meters per hour. The digestion tanks 2937 and 2950 preferably have capacities of 124 and 58.5 cubic meters, respectively. Holding tank 2957 preferably has a capacity of approximately 58.5 cubic meters. Hydrocyclones 2932, 2946, and 2956 preferably have a capacity of approximately 105 cubic meters per hour.

The rotors within prefractionation reactors 2901-2904 and digestion reactor 2934 preferably rotate with a rotational speed of approximately 1100 revolutions per minute. The rotors within fractionation reactors 2907, 2908, and 2909, germ and fiber reactor 2914, digestion reactors 2918, 2920, 2921, 2924, 2929, 2931, 2936, 2944a, and 2945, and recirculation pumps 2926, 2938, 2939, and 2942 preferably rotate with a rotational speed of approximately 1800 revolutions per minute.

Prefractionation reactors 2901-2904 preferably have a flow rate of approximately 155 tons per hour. Fractionation reactors 2907-2909 and germ and fiber reactor 2914 preferably have a flow rate of approximately 160 tons per hour. Digestion reactors 2920 and 2921 preferably have a flow rate of approximately 30 tons per hour. Digestion reactor 2918 preferably has a flow rate of approximately 105 tons per hour. Digestion reactors 2929 and 2931 preferably have a flow rate of approximately 102 tons per hour. Digestion reactors 2934, 2936, 2945, 2944a, 2948, 2949a, 2953, 2955, and 2959 preferably have a flow rate of approximately 105 cubic meters per hour.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A grain processing method, comprising:
   mixing the grain with fluid;
   inducing cavitation within the fluid to at least partially separate the grain;
   fractionating the grain with at least one fractionation reactor that is operable to separate the grain into pericarp, germ, and endosperm by simultaneously inducing cavitation within the fluid, inducing abrasion between the grain and the fluid, inducing abrasion between the grain, impacting the grain with protrusions, and subjecting the grain to a centrifugal force;
   dividing the separated biomass pericarp, germ, endosperm, and fluid into a first stream of pericarp and germ and a second stream of endosperm with fluid so that the first stream and second stream are separate from each other; and after the step of dividing the separated pericarp, germ, endosperm, and fluid, separating starch and protein within the endosperm in the second stream on a molecular level by: increasing the acidity of the fluid and endosperm; heating the fluid and endosperm; and passing the fluid and endosperm through at least one digestion reactor.

2. The method of claim 1, further comprising washing the grain before mixing it with fluid.

3. The method of claim 1, wherein the fluid is water.

4. The method of claim 1, wherein the step of inducing cavitation within the fluid is performed by at least one prefractionation reactor.

5. The method of claim 1, further comprising sanitizing the grain by cleaning the grain with pressurized water and ozonized water before the step of fractionating the grain.

6. The method of claim 1, wherein the step of fractionating the grain is carried out by a plurality of fractionation reactors that in combination are operable to separate the grain.

7. The method of claim 6, wherein said plurality of fractionation reactors are operable to separate the grain by inducing cavitation within the fluid and inducing abrasion between the grain and the fluid.

8. The method of claim 1, further comprising a fractionation vat that contains fluid and a fluid level sensor that monitors the fluid level within the fractionation vat, wherein the fractionation reactor comprises an inlet that receives fluid from within the fractionation vat and the grain.

9. The method of claim 1, wherein a hydrocyclone divides the separated pericarp, germ, endosperm, and fluid.

10. The method of claim 1, further comprising:
passing the endosperm and fluid through at least one reactor to promote separation of the endosperm on a molecular level after dividing the separated pericarp, germ, endosperm, and fluid; and
transferring the endosperm and fluid to a predigestion tank.

11. The method of claim 10, wherein the temperature of the endosperm and fluid within the predigestion tank is between approximately 30 to 52 degrees Celsius.

12. The method of claim 11, further comprising a heat exchanger in fluid communication with the predigestion tank that maintains the temperature of the endosperm and fluid at approximately 51 degrees Celsius.

13. The method of claim 1, wherein the fluid and endosperm are heated to a temperature of between approximately 30 to 52 degrees Celsius.

14. The method of claim 13, wherein the fluid and endosperm are heated to a temperature of approximately 51 degrees Celsius.

15. The method of claim 1, wherein the acidity of the fluid and endosperm is increased to a pH of between approximately 2 to 6.

16. The method of claim 15, wherein the acidity of the fluid and endosperm is increased to a pH of approximately 3.8.

17. The method of claim 1, wherein sulfur dioxide gas increases the acidity of the fluid and endosperm.

18. The method of claim 1, wherein the acidity of the endosperm and fluid is increased in a first sulfur tower.

19. The method of claim 18, wherein said step of separating the endosperm on a molecular level comprises passing the fluid and endosperm through a first plurality of digestion reactors.

20. The method of claim 19, further comprising transferring the fluid and endosperm to a first digestion tank after they are passed through said first plurality of digestion reactors.

21. The method of claim 20, further comprising:
transferring the fluid and endosperm to a second sulfur tower that increases the acidity of the fluid and endosperm;
transferring the fluid and endosperm to a second plurality of digestion reactors; and
transferring the fluid and endosperm to a second digestion tank.

22. The method of claim 21, further comprising:
transferring the fluid and endosperm from said second digestion tank to at least one reactor and at least one heat exchanger; and
transferring the fluid and endosperm into a holding tank.

23. The method of claim 22, wherein the temperature of the endosperm and fluid within the first and second digestion tanks is between approximately 30 to 52 degrees Celsius.

24. The method of claim 23, further comprising a heat exchanger in fluid communication with at least one of the first and second digestion tanks that maintains the temperature of the endosperm and fluid at approximately 51 degrees Celsius.

25. The method of claim 24, wherein each of the first and second digestion tanks includes a hot water jacket for maintaining the temperature of the endosperm and fluid.

26. The method of claim 22, wherein the temperature of the endosperm and fluid within the holding tank is between approximately 30 to 52 degrees Celsius.

27. The method of claim 26, wherein the holding tank includes a hot water jacket to maintain the temperature of the endosperm and fluid at approximately 51 degrees Celsius.

28. The method of claim 1, further comprising drying the pericarp and germ after the step of dividing the separated pericarp, germ, endosperm, and fluid.

29. The method of claim 1, wherein said fractionation reactor comprises:
a housing presenting a chamber having an inlet, an outlet, and a shaft opening;
a shaft projecting through said opening;
a rotor coupled with said shaft inside said chamber; and
a plurality of protrusions extending from said rotor, and
wherein said step of fractionating the grain comprises:
sending the grain and fluid through said inlet; and
rotating said rotor to separate the grain.

30. The method of claim 29, wherein said protrusions are spaced approximately equidistant from a center of said rotor, wherein adjacent protrusions abut each other, said protrusions comprising first and second sets of alternating protrusions having first and second heights, respectively, the first height being greater than the second height.

31. The method of claim 29, wherein said protrusions comprise a first row spaced approximately equidistant from a center of said rotor, a second row spaced approximately equidistant from said first row, and a third row spaced approximately equidistant from said second row, wherein said protrusions in each of said rows are spaced apart no less than approximately 6 millimeters.

32. The method of claim 31, wherein said housing presents first and second end walls and a side wall defining said chamber, wherein said inlet is in said first end wall, said shaft opening is in said second end wall, and said outlet is in said side wall, wherein said rotor presents a front surface facing said inlet and said plurality of protrusions extend from said front surface of said rotor toward said inlet, and wherein a plurality of protrusions extend from said first end wall of said housing toward said rotor between said first and second rows on said rotor.

33. The method of claim 4, wherein said prefractionation reactor comprises a housing presenting a chamber having an inlet, an outlet, and a shaft opening; a shaft projecting through said opening; a rotor coupled with said shaft inside said chamber; and a plurality of protrusions extending from said rotor, wherein the protrusions comprise a first row spaced approximately equidistant from a center of said rotor, a second row spaced approximately equidistant from said first row, and a third row spaced approximately equidistant from said second row, said protrusions having a generally C-shaped top profile.

34. The method of claim 33, wherein said housing presents first and second end walls and a side wall defining said chamber, wherein said inlet is in said first end wall, said shaft opening is in said second end wall, and said outlet is in said side wall, wherein said rotor presents a front surface facing said inlet and said plurality of protrusions extend from said front surface of said rotor toward said inlet, and wherein a plurality of grooves are formed in said first end wall of said housing facing said rotor.

35. A grain processing method, comprising:
mixing the grain with fluid;
inducing cavitation within the fluid to at least partially separate the grain;
fractionating the grain with at least one fractionation reactor that is operable to separate the grain into testa and cotyledon by simultaneously inducing cavitation within the fluid, inducing abrasion between the grain and the fluid, inducing abrasion between the grain, impacting the grain with protrusions, and subjecting the grain to a centrifugal force;
dividing the separated testa, cotyledon, and fluid into a first stream of testa and a second stream of cotyledon with fluid so that the first stream and second stream are separate from each other; and
after the step of dividing the separated testa, cotyledon, and fluid, separating starch and protein within the cotyledon in the second stream on a molecular level by: increasing the acidity of the fluid and cotyledon; heating the fluid and cotyledon; and passing the fluid and cotyledon through at least one digestion reactor.

36. A grain processing method, comprising:
mixing the grain with fluid;
inducing cavitation within the fluid to at least partially separate the grain;
fractionating the grain with at least one fractionation reactor that is operable to separate the grain into fiber and starch with protein by simultaneously inducing cavitation within the fluid, inducing abrasion between the grain and the fluid, inducing abrasion between the grain, impacting the grain with protrusions, and subjecting the grain to a centrifugal force;
dividing the separated fiber, starch with protein, and fluid into a first stream of fiber and a second stream of starch with protein and fluid so that the first stream and second stream are separate from each other; and
after the step of dividing the separated fiber, starch with protein, and fluid, separating the starch with protein in the second stream on a molecular level by: increasing the acidity of the fluid and starch with protein; heating the fluid and starch with protein; and passing the fluid and starch with protein through at least one digestion reactor.

* * * * *